United States Patent
Wagner et al.

(10) Patent No.: US 10,513,520 B2
(45) Date of Patent: Dec. 24, 2019

(54) SULFAMIDE AND SULFAMATE INHIBITORS OF HHINT1

(71) Applicant: Regents of the University of Minnesota, Minneapolis, MN (US)

(72) Inventors: Carston R. Wagner, St. Paul, MN (US); Rachit Shah, Minneapolis, MN (US)

(73) Assignee: Regents of the University of Minnesota, Minneapolis, MN (US)

(*) Notice: Subject to any disclaimer, the term of this patent is extended or adjusted under 35 U.S.C. 154(b) by 0 days.

(21) Appl. No.: 15/673,297

(22) Filed: Aug. 9, 2017

(65) Prior Publication Data

US 2018/0065965 A1  Mar. 8, 2018

Related U.S. Application Data

(60) Provisional application No. 62/372,630, filed on Aug. 9, 2016.

(51) Int. Cl.
| | |
|---|---|
| *C07D 473/18* | (2006.01) |
| *C07D 473/34* | (2006.01) |
| *C07D 405/14* | (2006.01) |

(52) U.S. Cl.
CPC ......... *C07D 473/34* (2013.01); *C07D 405/14* (2013.01); *C07D 473/18* (2013.01)

(58) Field of Classification Search
CPC ............................ C07D 473/18; C07D 473/34
See application file for complete search history.

(56) References Cited

FOREIGN PATENT DOCUMENTS

WO  WO-2017059411 A1 * 4/2017

OTHER PUBLICATIONS

Castro-Pichel et el. Arch.Pharm. vol. 322, pp. 11-15 (1989).*
Shah et al. ACS Med. Chem. Lett. 2016, 7, 780-784 and Supporting Information (13 pages).*
Bockman et al. J. Med. Chem. 2015, 58, 7349-7369.*
Davis et al. ACS Chem. Biol. 2014, 9, 2535-2544 and Supporting Information (p. S1-S61).*

* cited by examiner

*Primary Examiner* — Emily A Bernhardt
(74) *Attorney, Agent, or Firm* — Schwegman Lundberg & Woessner, P.A.

(57) ABSTRACT

Embodiments provide, among things, compounds of the formula I:

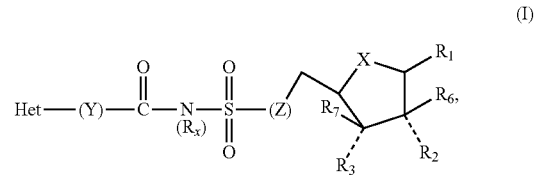

wherein Het, Y, $R_x$, Z, X, $R_1$-$R_3$, $R_6$, and $R_7$ are defined herein; and methods for using such compounds to reduce pain (e.g., neuronal pain), treat a mammal's addiction to nicotine or anti-pain drugs, and increase a mammal's sensitivity to drugs that bind MOR or NMDAR.

9 Claims, 4 Drawing Sheets

SULFAMIDE AND SULFAMATE INHIBITORS OF HHINT1

CROSS-REFERENCE TO RELATED APPLICATIONS

This application claims the benefit of U.S. Provisional Appl. Ser. No. 62/372,630, filed Aug. 9, 2016, which is incorporated by reference as if fully set forth herein.

STATEMENT OF U.S. GOVERNMENT SUPPORT

This invention was made with government support under CA 125360 awarded by the National Institutes of Health. The government has certain rights in the invention.

BACKGROUND

Human histidine triad nucleotide binding protein 1 (hHint1) has emerged as a target of interest due to its involvement in the regulation of a broad range of CNS functions, including opiate signaling, tolerance, neuropathic pain and nicotine dependence.[1,2] Human hHint1 belongs to the histidine triad (HIT) superfamily which are characterized by their conserved sequence motif, His-X-His-X-His-XX, where X is a hydrophobic residue. Human hHint1 exists as a homodimer and possesses nucleoside phosphoramidase and acyl-AMP hydrolase activity, with a substrate preference for purine over pyrimidine nucleosides.[3] Structural and kinetic studies have shown that hHint1 possess two identical and independent nucleotide-binding subunits.[4-6] Each monomer consists of two alpha helices. A conserved string of hydrophobic residues in or adjacent to the β-sheets creates a binding pocket (S1) for the nucleobase, while the aspartate (43) residue anchors the ribose sugar. The α-monophosphate group interacts with a conserved string of polar residues including the partially positive His114 and the nucleophilic His112 in the active site.

The side chains of the nucleoside phosphoramidates or acyl-AMP can occupy a relative shallow and solvent accessible pocket containing the only tryptophan residue in hHint1. A nucleophilic histidine (His112) residue forming part of the active site triad of hHint1 is responsible for the catalysis. A detailed investigation of the kinetic mechanism of hHint1 has revealed that the mechanism proceeds by rapid formation of the nucleotidylated-His intermediate, followed by partially rate limiting, water mediated hydrolysis and subsequent release of the nucleoside monophosphate from the active site.[5] The nucleoside phosphoramidase activity of hHint1 has been shown to be necessary for the activation of several preclinical and clinically approved antiviral and anticancer phsophramidate pronucleotides.[7-10] In addition, Chou and Wagner et al. have demonstrated that lysyl t-RNA synthetase generated lysyl-AMP is also a substrate for hHint1 in vitro.[11]

Hint proteins are highly conserved across all the kingdoms of life, suggesting that they have an important biological function. Hint1 has been implicated in the regulation of MITF/USF2 transcriptional activation complex in mast cells,[12] t-RNA synthetase amino acid adenylation,[11] apoptosis[13] and tumorigenicity.[14]

Hint1 is widely expressed in the region of brain primarily responsible for the modulation of pain [periaquaductal grey area (PAG)], addiction properties (nucleus accumbens) and the motor and sensory functions (cerebral cortex).[1] In agreement with these results, alterations in gene function or aberrant expression of hHint1 have been found in the brain tissues of clinical patients suffering from schizophrenia and bipolar disorders.[15] Moreover, Hint1-/- mice have been shown to exhibit hypersensitivity to amphetamine and decreased dependence on nicotine in self-administration studies.[16,17]

In addition, the NMDAR mediated feedback inhibition of the analgesic response has been demonstrated to be critically dependent on the co-association of Hint1 with MOR and NMDAR.[18] Hence, Hint1-/- mice have shown to display an enhanced analgesic response Δδ=1.11 ppm indicating that nucleobase recognition maybe a key event in driving the molecular recognition of nucleotide based ligands by Hint1.

Given its involvement in, among other things, apoptosis, tumorigenicity, and pain modulation, new agents are desirable for the modulation (e.g., inhibition) of hHint1.

SUMMARY

Chemical genetics is a powerful approach to elucidate biological functions of genes or proteins of interest using screens of diverse and targeted small molecules. Screening small molecular libraries for a compound that induces a phenotype of interest represents forward chemical genetics, whereas the reverse approach uses small molecules targeted to a protein or gene of interest, to probe their biological function.[20] Both approaches offer particular advantages of reversibility and the potential to modulate a single function. Recently, a non-hydrolyzable analog for hHint1 (compound 3, see FIG. 1a(3)), has been prepared by replacing the acyl-adenylate or phosphoramidate backbone in the substrate (compound 1 and 2, see FIG. 1a(1,2)) with a carbamate linker to yield compound 3. Compound 3 inhibits hHint1 with a low micromolar binding affinity ($K_d$=3.65±1.0 μM).[2] Using reverse chemical genetics, it was demonstrated that compound 3 not only enhances morphine analgesia, but also rescues and prevents the development of NMDAR mediated morphine tolerance in mice.[2] Importantly, the increase in the analgesic response and reduction in morphine tolerance were only observed in the wild type mice and not in Hint1-/- animals.[2] Thus, compound 3 acts as a selective modulator of Hint1 in vivo. Moreover, a single dose of 3 was able to reduce mechanical allodynia in animals for several days. Nevertheless, compound 3 suffers from poor solubility and low micromolar binding affinity for hHint1.

The disclosure provides compounds of formula I:

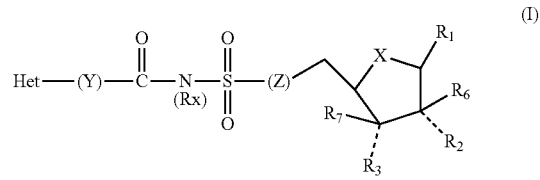

wherein:
$R_1$ is adenine, guanine, cytosine, thymine, 3-deazadenine or [6,7-imino(alkylene)] adenine, optionally substituted by 1, 2 or 3 U wherein each U is independently halo, hydroxy, ($C_1$-$C_6$)alkyl, ($C_3$-$C_6$)cycloalkyl, ($C_1$-$C_6$)alkoxy, ($C_3$-$C_6$)cycloalkyloxy, ($C_1$-$C_6$)alkanoyl, ($C_1$-$C_6$)alkanoyloxy, trifluoromethyl, hydroxy($C_1$-$C_6$)alkyl, —($CH_2$)$_{1-4}$P(=O)(OR$_w$)$_2$ aryl, aryl($C_1$-$C_6$)alkyl, or NR$_x$R$_y$;

$R_2$, $R_3$, $R_6$ and $R_7$ are each independently hydrogen, halo, hydroxy, ($C_1$-$C_6$)alkyl, ($C_3$-$C_6$)cycloalkyl, ($C_1$-$C_6$)alkoxy, ($C_3$-$C_6$)cycloalkyloxy, ($C_1$-$C_6$)alkanoyl, ($C_1$-$C_6$)alkanoyloxy, trifluoromethyl, azido, cyano, —N($R_z$)C(=O)N($R_{aa}$)($R_{ab}$), —N($R_z$)C(=O)O$R_{ac}$, or N$R_{ad}R_{ae}$, provided that one of $R_2$ and $R_6$ is hydroxy halo, ($C_1$-$C_6$)alkoxy, ($C_3$-$C_6$)cycloalkyloxy, trifluoromethyl, cyano, or N$R_{ad}R_{ae}$;

X is oxy, thio, or methylene;

Z is N(Rx) or O;

Y is ($C_1$-$C_6$)alkyl, and may contain 1-3 CH=CH moieties and/or 1-3 —O—, N(Rx) or —SO— moieties;

each $R_w$ is independently hydrogen or ($C_1$-$C_6$)alkyl;

$R_x$, $R_y$ and $R_z$ are each independently hydrogen, ($C_1$-$C_6$)alkyl, ($C_3$-$C_6$)cycloalkyl, phenyl, benzyl, phenethyl, or ($C_1$-$C_6$)alkanoyl; or $R_x$ and $R_y$ together with the nitrogen to which they are attached are pyrrolidino, piperidino or morpholino;

$R_{aa}$ and $R_{ab}$ are each independently hydrogen, ($C_1$-$C_6$)alkyl, ($C_3$-$C_6$)cycloalkyl, phenyl, benzyl, or phenethyl; or $R_{aa}$ and $R_{ab}$ together with the nitrogen to which they are attached are pyrrolidino, piperidino or morpholino;

$R_{ac}$, $R_{ad}$, and $R_{ae}$ are independently hydrogen, ($C_1$-$C_6$)alkyl, ($C_3$-$C_6$)cycloalkyl, phenyl, benzyl, or phenethyl;

wherein any ($C_1$-$C_6$)alkyl of $R_1$, $R_2$, $R_3$, $R_6$, $R_7$, $R_w$, $R_x$, $R_y$, $R_z$, $R_{aa}$, $R_{ab}$, $R_{ac}$, $R_{ad}$, and $R_{ae}$ is optionally substituted with one or more (e.g. 1, 2, 3, or 4) halo, hydroxy, ($C_1$-$C_6$)alkoxy, ($C_3$-$C_6$)cycloalkyloxy, ($C_1$-$C_6$)alkanoyl, ($C_1$-$C_6$)alkanoyloxy, trifluoromethyl, azido, cyano, oxo (=O), ($C_1$-$C_6$)alkyl, ($C_3$-$C_6$)cycloalkyl, ($C_3$-$C_6$)cycloalkyl($C_1$-$C_6$)alkyl, ($C_1$-$C_6$)alkyl-S—($C_1$-$C_6$)alkyl-, aryl, Het, aryl($C_1$-$C_6$)alkyl, or Het ($C_1$-$C_6$)alkyl, or N$R_{aj}R_{ak}$; wherein each $R_{aj}$ and $R_{ak}$ is independently hydrogen, ($C_1$-$C_6$)alkyl, ($C_3$-$C_6$)cycloalkyl, phenyl, benzyl, or phenethyl;

wherein Het is ($C_1$-$C_6$) alkyl, ($C_3$-$C_6$)cycloalkyl, or is a radical of a monocyclic, bicyclic, or tricyclic ring comprising about 3-20 atoms, including one or more carbon atoms and one or more heteroatoms selected from —O—, —S— and N(X) wherein X is absent or is H, O, phenyl or benzo, wherein 1, 2 or 3 ring carbons of Het can optionally be substituted with oxo;

wherein aryl is a phenyl radical or an ortho fused bicyclic carbocyclic radical having about 9 to 10 ring atoms in which at least one ring is aromatic;

and wherein any aryl or Het may optionally be substituted with one or more substituents selected from the group consisting of halo, hydroxy, ($C_1$-$C_6$)alkyl, ($C_3$-$C_6$)cycloalkyl, ($C_1$-$C_6$)alkoxy, ($C_3$-$C_6$)cycloalkyloxy, ($C_1$-$C_6$)alkanoyl, ($C_1$-$C_6$)alkanoyloxy, trifluoromethyl, trifluoromethoxy, nitro, cyano, and amino;

or a pharmaceutically acceptable salt thereof.

The disclosure provides compounds of formula I:

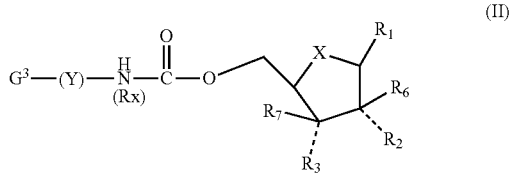

(II)

wherein:

$R_1$ is adenine, guanine, cytosine, thymine, 3-deazadenine or [6,7-imino(alkylene)] adenine, optionally substituted by 1, 2 or 3 U wherein each U is independently halo, hydroxy, ($C_1$-$C_6$)alkyl, ($C_3$-$C_6$)cycloalkyl, ($C_1$-$C_6$)alkoxy, ($C_3$-$C_6$)cycloalkyloxy, ($C_1$-$C_6$)alkanoyl, ($C_1$-$C_6$)alkanoyloxy, trifluoromethyl, hydroxy($C_1$-$C_6$)alkyl, —($CH_2$)$_{1-4}$P(=O)(O$R_w$)$_2$ aryl, aryl($C_1$-$C_6$)alkyl, or N$R_xR_y$;

$R_2$, $R_3$, $R_6$ and $R_7$ are each independently hydrogen, halo, hydroxy, ($C_1$-$C_6$)alkyl, ($C_3$-$C_6$)cycloalkyl, ($C_1$-$C_6$)alkoxy, ($C_3$-$C_6$)cycloalkyloxy, ($C_1$-$C_6$)alkanoyl, ($C_1$-$C_6$)alkanoyloxy, trifluoromethyl, azido, cyano, —N($R_z$)C(=O)N($R_{aa}$)($R_{ab}$), —N($R_z$)C(=O)O$R_{ac}$, or N$R_{ad}R_{ae}$, provided that one of $R_2$ and $R_6$ is hydroxy halo, ($C_1$-$C_6$)alkoxy, ($C_3$-$C_6$)cycloalkyloxy, trifluoromethyl, cyano, or N$R_{ad}R_{ae}$;

X is oxy, thio, or methylene;

Y is ($C_1$-$C_6$)alkyl, and may contain 1-3 CH=CH moieties and/or 1-3 —O—, N($R_x$) or —SO— moieties;

each $R_w$ is independently hydrogen or ($C_1$-$C_6$)alkyl;

$R_x$, $R_y$ and $R_z$ are each independently hydrogen, ($C_1$-$C_6$)alkyl, ($C_3$-$C_6$)cycloalkyl, phenyl, benzyl, phenethyl, or ($C_1$-$C_6$)alkanoyl; or $R_x$ and $R_y$ together with the nitrogen to which they are attached are pyrrolidino, piperidino or morpholino;

$R_{aa}$ and $R_{ab}$ are each independently hydrogen, ($C_1$-$C_6$)alkyl, ($C_3$-$C_6$)cycloalkyl, phenyl, benzyl, or phenethyl; or $R_{aa}$ and $R_{ab}$ together with the nitrogen to which they are attached are pyrrolidino, piperidino or morpholino;

$R_{ac}$, $R_{ad}$, and $R_{ae}$ are independently hydrogen, ($C_1$-$C_6$)alkyl, ($C_3$-$C_6$)cycloalkyl, phenyl, benzyl, or phenethyl;

$G^3$ is Het or H;

wherein any ($C_1$-$C_6$)alkyl of $R_1$, $R_2$, $R_3$, $R_6$, $R_7$, $R_w$, $R_x$, $R_y$, $R_z$, $R_{aa}$, $R_{ab}$, $R_{ac}$, $R_{ad}$, and $R_{ae}$ is optionally substituted with one or more (e.g. 1, 2, 3, or 4) halo, hydroxy, ($C_1$-$C_6$)alkoxy, ($C_3$-$C_6$)cycloalkyloxy, ($C_1$-$C_6$)alkanoyl, ($C_1$-$C_6$)alkanoyloxy, trifluoromethyl, azido, cyano, oxo (=O), ($C_1$-$C_6$)alkyl, ($C_3$-$C_6$)cycloalkyl, ($C_3$-$C_6$)cycloalkyl($C_1$-$C_6$)alkyl, ($C_1$-$C_6$)alkyl-S—($C_1$-$C_6$)alkyl-, aryl, Het, aryl($C_1$-$C_6$)alkyl, or Het ($C_1$-$C_6$)alkyl, or N$R_{aj}R_{ak}$; wherein each $R_{aj}$ and $R_{ak}$ is independently hydrogen, ($C_1$-$C_6$)alkyl, ($C_3$-$C_6$)cycloalkyl, phenyl, benzyl, or phenethyl;

wherein Het is ($C_1$-$C_6$) alkyl, ($C_3$-$C_6$)cycloalkyl, or is a radical of a monocyclic, bicyclic, or tricyclic ring comprising about 3-20 atoms, including one or more carbon atoms and one or more heteroatoms selected from —O—, —S— and N(X) wherein X is absent or is H, O, phenyl or benzo, wherein 1, 2 or 3 ring carbons of Het can optionally be substituted with oxo;

wherein aryl is a phenyl radical or an ortho fused bicyclic carbocyclic radical having about 9 to 10 ring atoms in which at least one ring is aromatic;

and wherein any aryl or Het may optionally be substituted with one or more substituents selected from the group consisting of halo, hydroxy, ($C_1$-$C_6$)alkyl, ($C_3$-$C_6$)cycloalkyl, ($C_1$-$C_6$)alkoxy, ($C_3$-$C_6$)cycloalkyloxy, ($C_1$-$C_6$)alkanoyl, ($C_1$-$C_6$)alkanoyloxy, trifluoromethyl, trifluoromethoxy, nitro, cyano, and amino;

or a pharmaceutically acceptable salt thereof.

A specific value for Z is N($R_x$), such as NH, or —O—.

A specific value for $R_1$ is adenine, quanine or [6,7-iminoethylene]adenine, wherein the imino moiety replaces the 6-amino group of adenine.

A specific value for X is O.

A specific value for Y is ($C_2$-$C_9$)alkyl. Het is defined in more detail below, and is preferably indolyl or substituted indolyl, e.g., indol-1-yl.

In some embodiments,

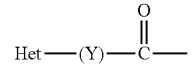

moieties are Heteroaryl[alkanoyl] moieties or alkanoyl moieties.

In one embodiment the disclosure provides a compound of formula (I); provided that $R_2$ and $R_3$ are each hydroxy when $R_1$ is adenine, guanine, cytosine, thymine, or uracil, preferably adenine or quanine, unsubstituted or substituted as disclosed above, X is oxy; $R_6$ is hydrogen, and $R_7$ is hydrogen.

The disclosure also provides a method for treating pain in an animal comprising administering an effective amount of a compound of formula I or a pharmaceutically acceptable salt thereof to an animal (e.g. a mammal) in need of such treatment.

The disclosure also provides a method for treating the state of addiction in an animal comprising administering an effective amount of a compound of formula I or a pharmaceutically acceptable salt thereof to an animal in need of such treatment.

The disclosure also provides a method for treating pain, including neuropathic pain such as allodynia, in an animal comprising administering an effective amount of at least one compound of formula I or a pharmaceutically acceptable salt thereof to an animal in need of such treatment.

The disclosure also provides a method for treating addiction such as that caused by compounds that can bind to MOR or NMDAR receptors comprising administering an effective amount of a compound of formula I or a pharmaceutically acceptable salt thereof to an animal in need of such treatment.

The disclosure also provides a method for treating nicotine or opioid addiction in an animal comprising administering an effective amount of a compound of formula I or a pharmaceutically acceptable salt thereof to an animal in need of such treatment.

The disclosure also provides the use of a compound of formula I or a pharmaceutically acceptable salt thereof to prepare a medicament for treating pain in a mammal.

The disclosure also provides the use of a compound of formula I or a pharmaceutically acceptable salt thereof to prepare a medicament for treating neuropathic pain.

The disclosure also provides the use of a compound of formula I or a pharmaceutically acceptable salt thereof to prepare a medicament for treating addiction of a mammal, e.g., a human.

The disclosure also provides the use of a compound of formula I or a pharmaceutically acceptable salt thereof to prepare a medicament to sensitize a mammal to anti-pain drugs that bind to MOR or NMDAR receptors.

DESCRIPTION

Figure 1A:
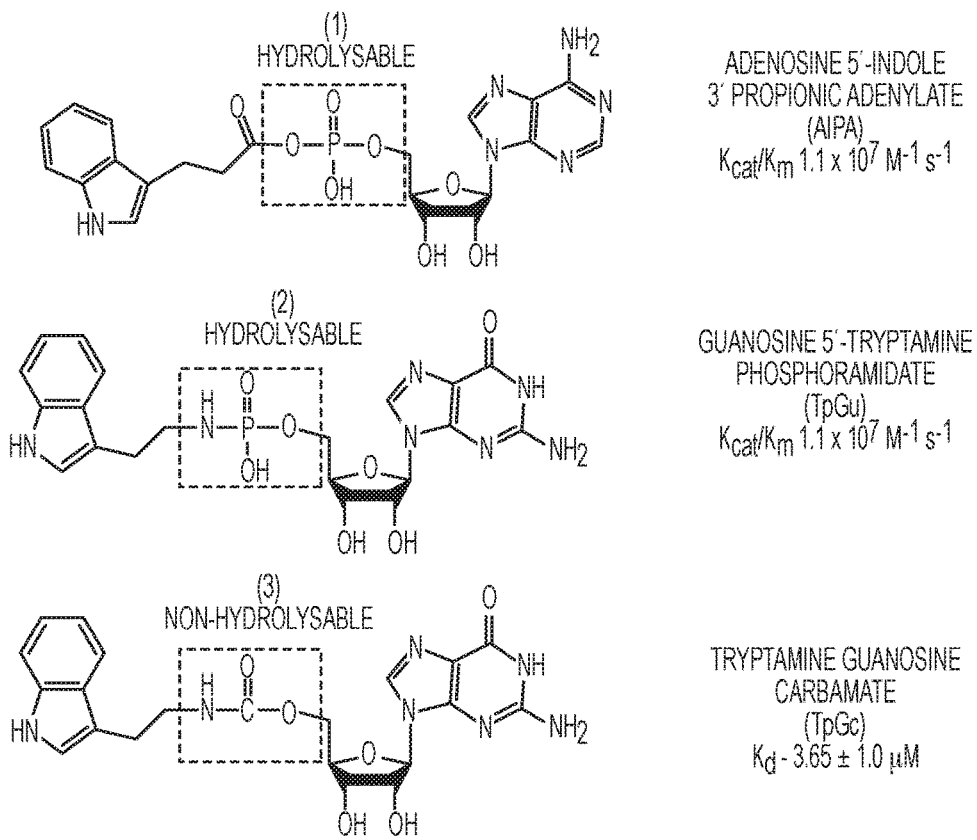
FIGS. 1A and 1B are, respectively, chemical structures of the hHint1 substrates (AIPA and TpGu) and a previously reported hHint1 inhibitor (TrpGc); and hHint1 inhibitors of the embodiments described herein, with an acyl-sulfamate or sulfamide backbone to improve solubility and potency over the TrpGc.

Reference will now be made in detail to certain embodiments of the disclosed subject matter, examples of which are illustrated in part in the accompanying drawing. While the disclosed subject matter will be described in conjunction with the enumerated claims, it will be understood that the exemplified subject matter is not intended to limit the claims to the disclosed subject matter.

The following definitions are used, unless otherwise described: halo is fluoro, chloro, bromo, or iodo. Alkyl, alkoxy, etc. denote both straight and branched groups; but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic. Het or Het$^1$ is (C1-C6)alkyl, (C3-C6)cycloalkyl or is a radical of a monocyclic, bicyclic, or tricyclic ring system containing a total of 3-20 atoms, including one or more (e.g., 1, 2, 3, 4, 5, 6, or 7) carbon atoms, and one or more (e.g., 1, 2, 3, 4, or 5) heteroatoms selected from oxygen, sulfur, and N(X) wherein X is absent or is H, O, $(C_1-C_4)$alkyl, phenyl or benzyl, wherein one or more ring carbons of Het can optionally be substituted with oxo (=O); Heteroaryl encompasses a radical attached via a ring carbon of an aromatic ring containing five or six ring atoms consisting of carbon and one to five heteroatoms each selected from the group consisting of non-peroxide oxygen, sulfur, and N(X$^1$) wherein X$^1$ is absent or is H, O, $(C_1-C_4)$alkyl, phenyl or benzyl, as well as a radical of an ortho-fused bicyclic or tricyclic heterocycle of about eight to ten ring atoms derived therefrom, particularly a benz-derivative or one derived by fusing an ethylene, e.g., 6,7- or 8,9-etheno-adenosine, propylene, trimethylene, or tetramethylene diradical thereto. The term Het encompasses Heteroaryl.

It will be appreciated by those skilled in the art that compounds described herein having a chiral center may exist in and be isolated in optically active and racemic forms. Some compounds may exhibit polymorphism. It is to be understood that the disclosure encompasses any racemic, optically-active, polymorphic, or stereoisomeric form, or mixtures thereof of a compound described herein, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine modulatory activity using the standard tests described herein, or using other similar tests which are well known in the art.

Specific values listed below for radicals, substituents, and ranges, are for illustration only; they do not exclude other defined values or other values within defined ranges for the radicals and substituents Specifically, $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl;

$(C_1-C_6)$alkoxy can be methoxy, ethoxy, propoxy, isopropoxy, butoxy, iso-butoxy, sec-butoxy, pentoxy, 3-pentoxy, or hexyloxy;

$(C_1-C_6)$alkanoyl can be acetyl, propanoyl or butanoyl; hydroxy$(C_1-C_6)$alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl;

$(C_2-C_6)$alkanoyloxy can be acetoxy, propanoyloxy, butanoyloxy, isobutanoyloxy, pentanoyloxy, or hexanoyloxy;

aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

A specific value for Het-Y is $(C_1-C_6)$alkyl substituted with Het and optionally substituted with one or more halo, hydroxy, $(C_1-C_6)$alkoxy, $(C_1-C_6)$alkanoyl, $(C_1-C_6)$alkanoyloxy, trifluoromethyl, cyano, or aryl.

A specific value for Het-Y is (C1-C9) alkyl or $(C_1-C_6)$ alkyl substituted with Het and optionally substituted with one or more aryl or Het.

A specific value for Het-Y— is $(C_1-C_6)$alkyl substituted with a pyridyl, indolyl, isoindolyl, furyl, thienyl, pyrrolyl, benzofuranyl, benzothienyl, imidazolyl, thiazoyl, pyrrolidinyl, piperidinyl, piperazinyl, or morpholino ring, which ring is optionally substituted with one or more substituents selected from the group consisting of halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, trifluoromethoxy, nitro, cyano, and amino.

A specific value for Het-Y is $(C_1-C_6)$alkyl substituted with an indolyl ring, which ring is optionally substituted with one or more substituents selected from the group consisting of halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, trifluoromethoxy, nitro, cyano, and amino.

A specific value for Het-Y— is $(C_1-C_6)$alkyl substituted with an indolyl ring.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made, as well as ammonium salts or quats.

The compounds of the disclosure can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula I in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

In some embodiments, the active ingredient is administered to achieve peak plasma concentrations of the active compound of from about 0.5 to about 75 $\mu$M, preferably, about 1 to 50 $\mu$M, most preferably, about 2 to about 30 $\mu$M. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The compounds described herein can generally be prepared using procedures similar to those described in U.S. Pat. No. 6,475,985.

The disclosure provides hydrolyzable nucleotide analogs for hHint1 that contain an acyl-sulfamate or acyl-sulfamide linker that mimics the corresponding phosphoramidate and acyl-phosphate moieties.

EXAMPLES

Embodiments of the disclosure will be further described by reference to the following detailed and non-limiting examples.

General

Guanosine was purchased from Acros Organics. Chloroacetaldehyde solution (50% wt in water), Triphenylphosphine (cat no: T84409-1004), Methyl triphenoxy phosphonium iodide (MTPI, cat no: 226432-10), Chlorosulfonyl Isocynate (cat no: 142662-254), Sulfamide (cat no: 277310) was purchased from Sigma-Aldrich. All solvents were purchased from Fischer Scientific and used as received unless otherwise noted. Anhydrous solvents such as DMF, Acetonitrile were used directly from solvent dispensing system (J. C. Meyer) packed with two columns of neutral alumina and dispensed under argon. DMA and Pyridine was purchased in a sure seal bottle from Sigma-Aldrich. Thin-layer chromatography was performed using EMD pre-coated silica gel 60 F-254 plates. All preparative separations were performed using Teledyne Isco combiflash system and using RediSepRf high performance gold silica pre-packed columns. Analytical HPLC for the stability studies were performed on Agilent C18 zorbax SB-Aq column (3.5 $\mu$m, 4.6×150 mm) using water (solvent A) and acetontrile (solvent B) with 0.1% TEA as additive. High-resolution mass spectrometry was performed LTQ Orbitrap Velos (Thermo Scientific™). Samples and compounds during synthesis were freeze-dried with a lyophilizer available from Labonaco. All $^1$H- and $^{13}$C-NMR spectra were collected in $d_6$-DMSO (Cambridge Isotope Laboratories, Cambridge, Mass.) at 25° C. using Ascend™ Bruker spectrometer 500 MHz at the Department of Medicinal Chemistry CCRB NMR facility at the University of Minnesota unless otherwise stated. All NMR chemical shifts were recorded in δ parts per million using $d_6$-DMSO as internal reference. Thermodynamic measurements for protein-ligand association were performed in 96-well plates (Nunc 260251 U96 DeepWell 96-Well×1.3 ml from thermo scientific) using MicroCal Auto-ITC$_{200}$ system (GE Healthcare life sciences). Nickel nitrilotriacetic acid (Ni-NTA) was purchased from Qiagen and cobalt column agarose from Thermofishcer Scientific. Biological buffers were purchased from Sigma-Aldrich. Protease inhibitor tablets were obtained from Roche.

Protein Expression and Purification

The full-length sequence of hHint1 was expressed from the pMCSG7 vector (N-terminal, tobacco etch virus (TEV) protease cleavable $His_6$ tag) in Rosetta2 pLysS cells. The cells were grown in 2×1 L LB (Fischer Scientific) media with ampicillin (100 mg/L, Sigma-Aldrich), chloramphenicol (34 mg/L, Sigma-Aldrich), and glucose (0.1% w/v, BD Difco) at 37° C. with shaking at 250 rpm. At $OD_{600}$=0.7, cultures were induced to a final concentration of 1 mM IPTG (Denville Scientific Inc) and incubated at 25° C. overnight. The cultures were harvested by centrifugation at 7,500 g at 4° C. for 10 min and the pellets were collected, then resuspended in buffer A (50 mM HEPES pH 7.0, 300 mM NaCl, 10% glycerol, 10 mM imidazole), which was then adjusted to 1 mg·mL$^{-1}$ lysozyme and Benzonase nuclease (20 ul). The resuspended cells were lysed by sonication (eight cycles of 30 s on, 30 s off) at 4° C. The cell debris was removed from the lysate by centrifugation at 16,000 g at 4° C. for 45 min. The supernatant was loaded onto a nickel affinity column, washed with buffer A, and then eluted with an imidazole gradient using buffer B (50 mM HEPES pH 7.0, 300 mM NaCl, 10% glycerol, 500 mm imidazole). Fractions containing desired protein was combined and to it was added N-terminally His-tagged TEV protease 2% (w/w). The resulting solutions was transferred to a dialysis tubing (molecular weight cut-off of 6000-7000 Da) and dialyzed against 2 L of TEV cleavage buffer (50 mM HEPES pH 7.0, 300 mM NaCl, 10% glycerol, 0.5 mM EDTA and 1 mM DTT) overnight at 4° C. The dialyzed protein was then buffer exchanged into buffer A and passed through cobalt affinity chromatography to remove TEV protease. The flow through obtained was concentrated to 5 mL and further purified using size exclusion chromatography (SEC buffer, 20 mM Tris pH 7.5, 150 mM NaCl, 10% glycerol). Pure fractions were collected and concentrated. The protein concentration was then determined using A280 absorbance in nanodrop using calculated extinction coefficient of 8480 M$^{-1}$ cm$^{-1}$ and molecular weight of 14000 Da. The final protein was stored in the stored at −80° C. until in use.

Isothermal Titration Calorimetry (ITC)

ITC experiments were conducted on a MicroCal Auto-ITC$_{200}$ system (GE Healthcare life sciences). All titration experiments were performed at 20° C. in ITC buffer (10 mM Tris, 150 mM NaCl, pH 7.5). hHint1 was exchanged into ITC buffer using Micro biospin6 columns (BioRad, USA) and final protein concentrations were determined as described above. To determine the dissociation constant of stock concentration (300-400 uM) of inhibitors was titrated with 15-20 uM of Hint1. Twenty injections of ligand were injected (injection volume 2 ul) into the protein cell. The resulting change in enthalpy was measured and the background heat of dilution was subtracted by performing similar experiments in the absence of inhibitors. The background heat of dilution was subtracted from the resulting data and was fitted into one-site binding model using the ITC$^{200}$ microcal software. The resulting association constant obtained by fitting the curve was converted into $K_d$ using $K_a$=1/$K_d$ relationship.

Analytical HPLC Studies to Determine the Stability of the Inhibitors.

Analytical studies were performed on a Beckman coulter system gold operated by Karat software, with an Agilent C18 Zorbax SBAq column (4.6×150 mm, 3.5 µm). Stock solutions (10 mM) of the inhibitors were prepared in a Tris buffer (10 mM Tris, 200 mM NaCl, pH 7.4). For stability studies, the stock solutions were diluted to a concentration of 50-100 uM using Phosphate Buffer Saline buffer (PBS) and incubated at 37° C. At indicated time points 200 ul aliquots of the sample volume were withdrawn and injected into the HPLC system for monitoring the stability and degradation of the compounds. The samples were eluted using the gradient of solvent A (Water) and B ($CH_3CN$) with a 0.1% triethylamine additive (0-4 min: gradient 0% B, 4-14 min: gradient 20% B, 14-29 min: gradient 80% B, flow rate 0.5 ml/min) with detection at 168-400 nm.

General Procedure for Acid-NHS Ester Preparations.

N-Hydroxysuccinimide (0.62 g, 0.0053 mol, 1.0 equiv.) followed by EDC (0.00795 mmol, 1.5 equiv.) was added to a solution of the respective acid (0.0053 mol, 1.0 equiv) in anhydrous THF (13 mL). The solution was stirred for 21 h at room temperature. The solvent was evaporated in vacuum and the resulting residue dissolved in ethylacetate (80 mL). The organic phase was washed with saturated $NaHCO_3$ (2×20 mL) and NaCl solution (2×20 mL), dried with $NaSO_4$, and filtered. The solvent was removed under vacuum to give crude NHS ester. The crude product was recrystallized with ethylacetate/petroleum ether to obtain the desired NHS esters below. The esters were used for coupling without any further purification. 1H and 13C NMR indicated relatively clean esters (see below).

Abbreviations

The following abbreviations are used herein:

hHint1, human histidine triad nucleotide binding protein 1;

NMDAR, N-methyl D-aspartate receptor;

MOR, mµ-opioid receptor;

CNS, Central Nervous System;

DBU, 1,8-Diazabicyclo[5.4.0] undec-7-ene;

TFA, Trifluoroacetic acid; MTPI, Methyltriphenoxyphosphonium Iodide;

DMA, Dimethyl Acetamide;

EDC, 1-Ethyl-3-(3-dimethylaminopropyl)carbodiimide.

The effect of a non-hydrolyzable nucleotide analog Bio-AMS was compared with compound 3 on the activity of hHint1 using a fluorescence assay described previously.[3]

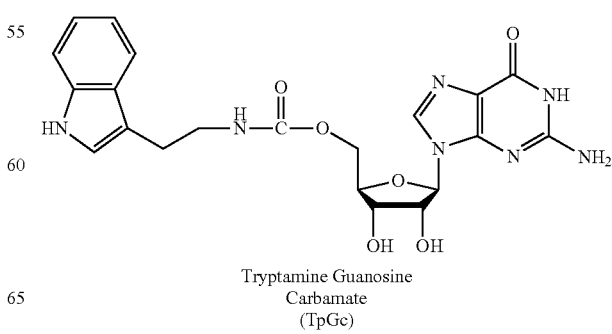

3

Tryptamine Guanosine Carbamate (TpGc)

At a fixed saturating substrate concentration, both Bio-AMS 5'-amino-5'-N-(biotinyl)sulfamoyl-5'-doxyadenosine and compound 3 exhibited a dose dependent decrease in the activity of hHint1 with maximum half inhibitory concentration ($IC_{50}$) values of 1.0±0.3 µM and 25.5±6.0 µM respectively. Isothermal titration calorimetry (ITC) was used to investigate the nature of non-covalent interactions on the inhibitory activity of Bio-AMS on hHint1. The ITC studies provided an experimental dissociation constant ($K_d$) of 0.32±0.1 µM with an n value of 1.0±0.1 indicating one binding site per hHint1 monomer. Bio-AMS was found to bind approximately 11 and 209 fold more tightly than compound 3 and guanosine monophosphate (GMP) respectively, and to be dominated by enthalpy and not entropy.

Figure 1B:
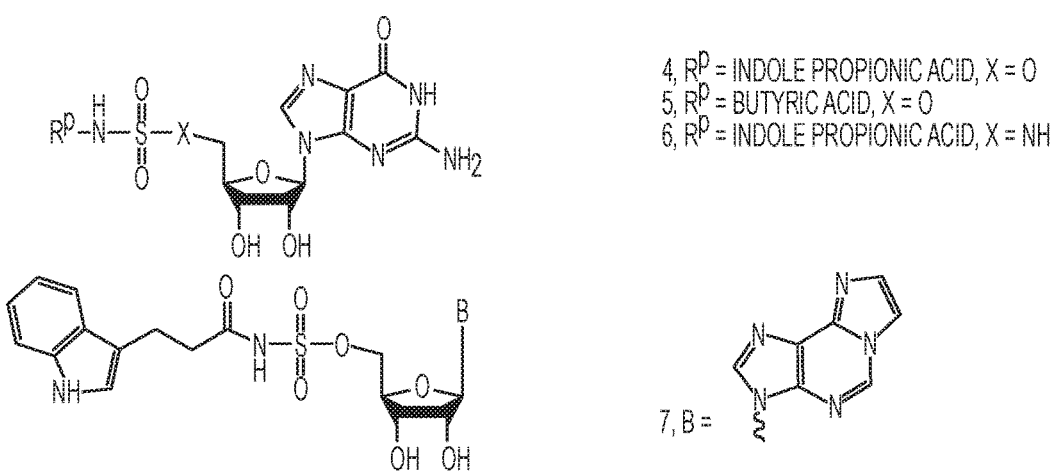

In order to avoid potential off target effects on enzymes utilizing adenosine and adenosine nucleotide based substrates, analogues of compound 3 containing an acyl-sulfamate or acyl-sulfamide backbone (see FIG. 1B) were developed. The first inhibitor examined was based on the replacement of the carbamate backbone in 3 with an acyl-sulfamate backbone. The synthesis of compound 4 (Scheme 1) began with 5'-OH sulfamoylation of 2',3'-O-isopropylidene guanosine (8) to provide intermediate 9. Coupling of 9 with the N-hydroxysuccinic acid ester of 3-indole propionic acid in the presence of DBU (1,8-Diazabicyclo[5.4.0]undec-7-ene) afforded 10. Deprotection of the acetonide in compound 10 with aqueous TFA yielded the final compound 4. In similar fashion compound 5 with a butyric acid side chain was synthesized.

identified key interactions between nucleoside monophosphates and mouse Hint1.[22] Their $^1$H-$^{15}$N HSQC investigations revealed large chemical shift perturbations (Δδ>0.2 ppm) for the residues surrounding the canopy holding the nucleobase and sugar upon addition of the nucleoside monophosphate. Isoleucine 44 in the S1 hydrophobic pocket exhibited the largest chemical shift difference of Δδ=1.11 ppm indicating that nucleobase recognition maybe a key event in driving the molecular recognition of nucleotide based ligands by Hint1.

The impact of a hydrophobic nucleoside inhibitor with an acyl-sulfamate backbone was explored by replacing the guanosine base in 4 with a tricyclic ethenoadenosine base. Compound 7 provides an additional advantage of stability towards cyclonucleoside formation when compared to an adenosine nucleobase due to the extensive delocalization of the N-3 nitrogen electrons into the tricyclic ring system. The synthesis of compound 7 (Scheme 2) began with the cyclization of exocyclic amine in 11 with chloroacetaldehyde in mildly acidic sodium acetate buffer at 40° C. to yield the fluorescent compound 12. The formation of 12 in the reaction mixture can be easily monitored on thin layer chromatography due to its fluorescent properties. Compound 12 was then treated with sulfamoyl chloride in the presence of triethylamine to yield compound 13. Coupling of 13 with the N-hydroxysuccinic acid ester of 3-indole propionic acid in the presence of DBU followed by deprotection of the acetonide with aqueous TFA yielded compound 7. To avoid potential decomposition due to the intrinsically acidic free acyl-sulfamate group, all the acyl-sulfamate compounds (4, 5 and 7) were prepared and purified as a triethylammonium

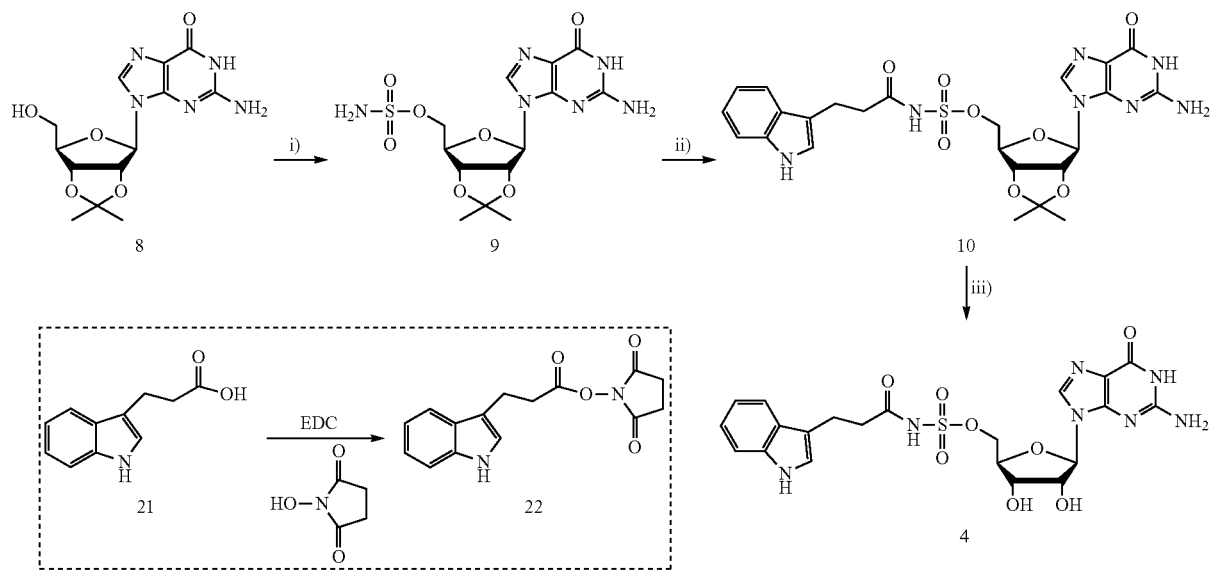

Scheme 1$^a$ $^a$Reagents and conditions: i) NH$_2$SO$_2$Cl, DMA, 85%; ii) 22, DBU, DMF 55%; iii) 80% aq. TFA Structural studies performed using x-ray crystallography or NMR provide an insight into the molecular recognition driving the interaction between a protein and a ligand. Using 2D-NMR studies, Shapiro and co-workers investigated and salt using reverse phase chromatography. Stability studies performed on all the compounds using high performance liquid chromatography (HPLC) revealed no cyclonucleoside formation at 37° C. over 48 h in phosphate buffered saline.

This result is in striking contrast to the previously reported rapid decomposition of the acyl-sulfamate analog of Bio-AMS via cyclonucleoside formation.[21]

Scheme 2[a]

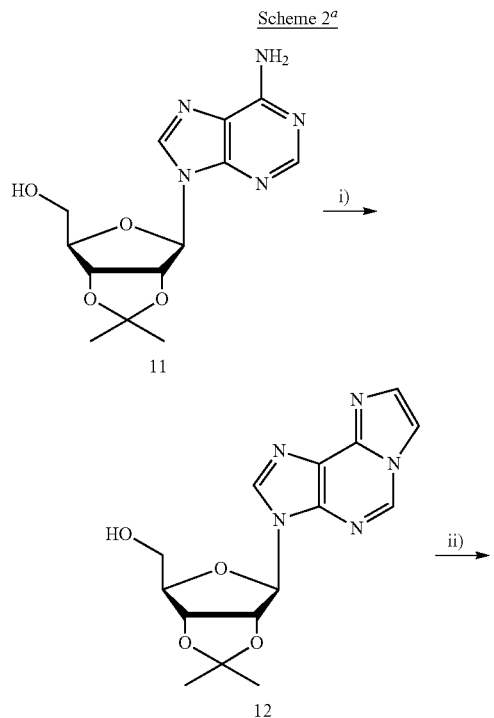

-continued

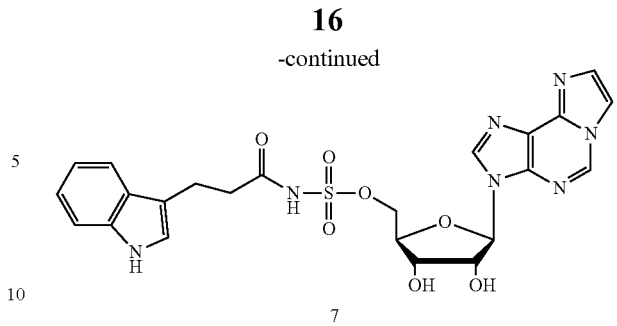

[a]Reagents and conditions: i) Chloroacetaldehyde, NaOAc 0.1M pH 6.5, 40° C., 30%; ii) NH$_2$SO$_2$Cl, DMA, 85%; iii) 22, DBU, overnight, 55%; and 80% aq. TFA, 1 hr quant.

Replacement of the 5'-oxygen atom in the acyl-sulfamate with a nitrogen affords an acyl-sulfamide backbone, which increases the pKa of the backbone NH by 2-3 units. The increased pKa has been shown to increase the stability and the binding affinity of Bio-AMS towards biotin protein ligase.[20] Hence, compound 6 was designed to investigate the impact of the enhanced negative charge of the backbone on the binding affinity of hHint1. The synthesis of compound 6 (Scheme 3) began with protection of the exocyclic nitrogen on compound 8 with N, N-dimethyl formamide dimethylacetal to yield N, N-dimethyl aminomethylene-2'-3'-O-isopropylidene guanosine (14). Iodination of the 5'-hydroxy group in 14 with methyltriphenoxyphosphonium iodide (MTPI) in a Moffat reaction afforded compound 14a (see supporting info). Displacement of the iodide in 14a with sodium azide followed by reduction under the Staudinger reaction conditions yielded compound 16 with a 5'-amine on the ribose sugar. Next, the corresponding 5'-amino nucleoside was converted to the 5'-sulfamide by refluxing compound 16 with sulfamide (NH$_2$SO$_2$NH$_2$) in 1,4-dioxane for 2 h.[23] Surprisingly, this step also resulted in the removal of the N, N-dimethyl aminomethylene of the exocyclic amine along with the formation of the desired product. The crude 5'-sulfamide nucleoside was then stirred in sodium hydroxide/methanol solution to completely deprotect the N, N-dimethyl aminomethylene group to afford 17 in an overall yield of 34% over two steps. Coupling of 17 to the N-hydroxysuccinic acid ester of 3-indole propionic acid in the presence of DBU followed by the deprotection of the acetonide with aqueous TFA (trifluoroacetic acid) yielded the final compound 6. All the compounds prepared above displayed superior aqueous solubility compared to compound 3. Stock solutions up to 5 mM for the guanosine analogues (compound 4, 5 and 6) and 20 mM for 7 were easily prepared in aqueous buffers.

Scheme 3[a]

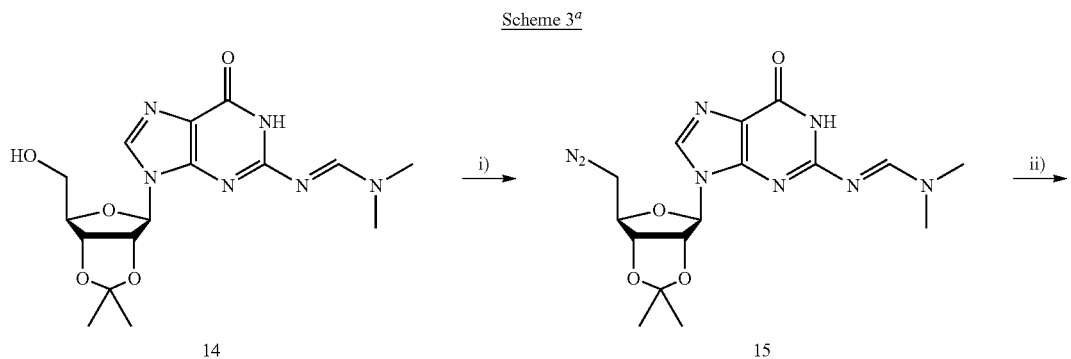

-continued

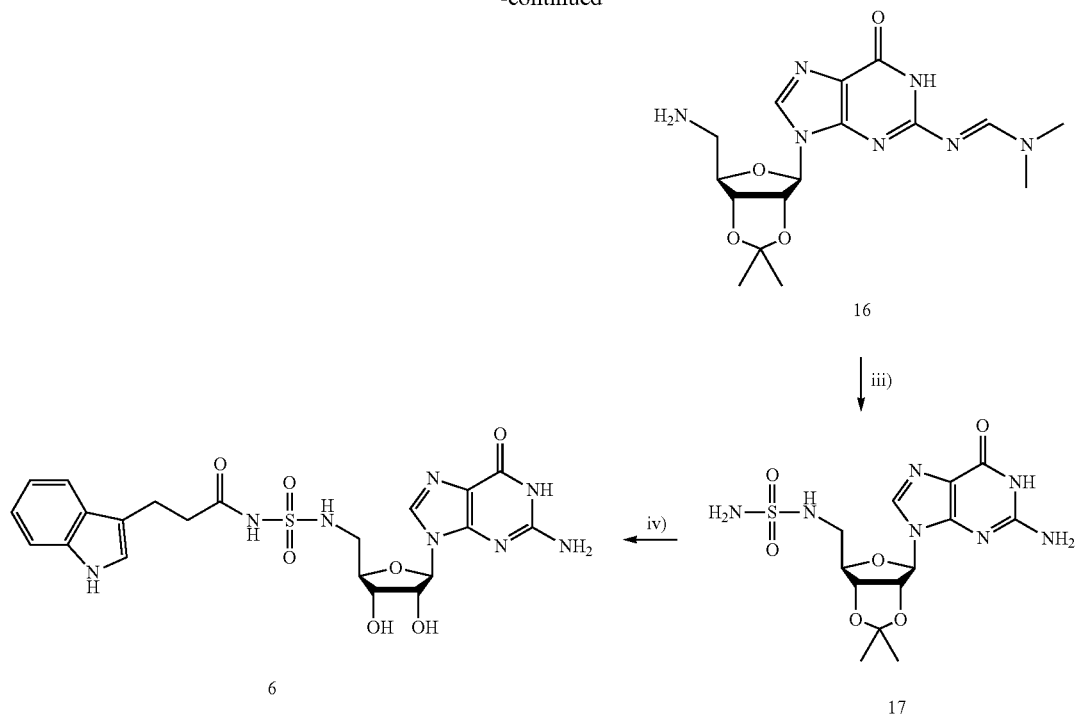

*a*Reagents and conditions: i) MTPI, THF, -70° C. for 30 min and then RT for 4 h 92%; ii) NaN₃, DMF, RT overnight, 55%; iii) Triphenyl phosphine aq dioxane, triethylamine, 50° C., 3 hrs, 54%; iii) NH₂SO₂NH₂, 1,4-dioxane reflux for 2 hrs; and 4N NaOH/MeOH for 2 h, 33%; iv) 22, DBU in DMF, overnight, 55%; and 80% aq. TFA, 1 hr quant.

The in vitro binding affinity of the new series was evaluated of analogues for hHint1 using isothermal calorimetry (ITC). In comparison to 3, compound 4 displayed a 4.5 fold increase in binding affinity with a measured dissociation constant of 0.81±0.11 μM for hHint1 (Table 1).

TABLE 1

Thermodynamic parameters and dissociation constants of hHint1-ligand complexes determined using ITC

| Compound | $K_d$ (μM) | ΔH, kcal mol$^{-1}$ | −TΔS, kcal mol$^{-1}$ | ΔG, kcal mol$^{-1}$ |
|---|---|---|---|---|
| 3[a] | 3.65 ± 1.00 | −13.54 ± 1.00 | 9.54 ± 4.17 | −4.1 ± 2.0 |
| 4 | 0.81 ± 0.11 | −16.51 ± 0.17 | 8.05 ± 0.88 | −8.46 ± 0.4 |
| 5 | 2.90 ± 0.25 | −13.59 ± 1.12 | 7.71 ± 0.27 | −5.81 ± 1.0 |
| 6 | 0.92 ± 0.07 | −14.75 ± 0.12 | 6.57 ± 0.17 | −8.24 ± 0.12 |
| 7 | 0.23 ± 0.01 | −17.31 ± 0.05 | 8.19 ± 0.13 | −9.13 ± 0.11 |
| GMP[b] | 67 ± 7.9 | — | — | — |

[a]Data adapted from previously published result by Garzon et al.[2]
[b]Data shown from the NMR titrations previously reported by Shapiro and co-workers.

The increased binding affinity of 4 is likely due to electrostatic and/or hydrogen-bonding interactions of the acyl-sulfamate backbone, with polar side chains in the active site, as indicated by the increased gain in the enthalpic component over 3.

Increasing the pKa of the backbone with a sulfamide in compound 6 did not alter the binding affinity of compound 1 as indicated by their similar dissociation constants. Attachment of an indole side chain intramolecularly to a nucleoside has been shown to dynamically quench the fluorescence of the indole side chain due to stacking interaction of the indole ring on the nucleobase.[24] Therefore, one might predict that compounds 4 and 5 are likely to encounter a higher entropic penalty upon binding to hHint1. Consequently, one might propose that removal of the indole group in compound 5 would likely increase the binding affinity by decreasing the entropic cost of binding to hHint1. Surprisingly, the dissociation constant for compound 5 for hHint1 was found to be in a 3-4 fold greater in comparison to 4 (Table 1). Comparing the thermodynamic parameters of 4 and 5 revealed no significant differences in the entropy of binding. However, compound 5 displayed a nearly 2 kcal mol$^{-1}$ decrease in the enthalpy of binding. These results indicate that increasing interactions associated with the active site can improve the ligand binding affinity.

Consistent with this observation, compound 7 in which a tricyclic nucleobase has been incorporated, resulted in an increased binding affinity with a measured dissociation constant of 0.23±0.01 μM. Compound 7 displayed an increase in binding affinity of 16 and 291 fold over compound 3 and GMP, respectively. In comparison with 4, a nearly 1 kcal mol$^{-1}$ increase in the enthalpy of binding was observed for 7, with no observable difference in the entropic component. These results indicate that, while ligand and active site desolvation is important the interactions of the ligand with the active site appear to dominate biomolecular recognition of the ligands by hHint1.

The compounds disclosed herein can permit the modulation of processes that are potentially regulated by HINT1 at the cell membrane, such as MOR-NMDAR cross-regulation. The ability of the HINT enzymatic inhibitor guanosine-5'-tryptamine carbamate (TpGc) (3)[2] on the capacity of morphine to promote antinociception and in the development of antinociceptive tolerance. The intra-cerebroventricular (icv), administration of TpGc to mice potentiated morphine-evoked antinociception and reduced the development of acute tolerance. A single icv administration of TpGc to mice suffering chronic constriction injury (CCI) led to a significant attenuation of mechanical allodynia that persisted for several days, suggesting a regulatory role for HINT1 in its interaction with NMDARs.

Based on the bioactvity of TpGc, it is believed that the compounds of formula I will exhibit similar beneficial results in other mammals, including humans. Therapeutically effective doses of the compounds of formula I can be derived from the amounts employed to reduce pain and tolerance, e.g., in compounds interacting with the μ ("mu") opioid receptor.

Synthesis of Inhibitors.

Example 1. Synthesis of 2,5-dioxopyrrolidin-1-yl-3-(1H-indol-3-yl) Propanoate (22)

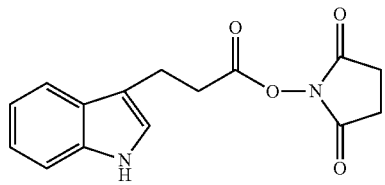 [SMILES: O=C(CCc1c[nH]c2ccccc12)ON1C(=O)CCC1=O]

Above NHS ester was prepared using general procedure above. The resulting compound was obtained in 46% yield. $^1$H NMR spectrum was (DMSO-d6): 2.82 (s, 4H), 3.05 (t, 4H), 6.99 (s, 1H), 7.09 (t, 1H), 7.22 (s, 1H), 7.36 (d, 1H), 7.56 (d, 1H) and 10.88 (s, 1H). $^{13}$C-DMSO-d6: 170.31, 168.68, 136.27, 126.68, 122.82, 121.07, 118.38, 118.37, 112.06, 111.48, 31.35, 25.62 and 19.89.

Example 2. Synthesis of 2,5-dioxopyrrolidin-1-yl-pentanoate (23)

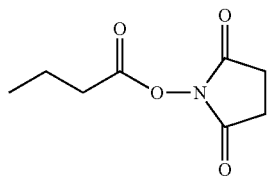

Above NHS ester was prepared using general procedure above. The resulting compound was obtained in 47% yield. $^1$H NMR spectrum was (DMSO-d6): 1.06 (t, 3H), 1.79 (q, 2H), 2.63 (s, 2H) and 2.82 (s, 4H). $^{13}$C-DMSO-d6: 172.00, 170.22, 33.47, 26.57, 19.24 and 13.68.

Example 3. Synthesis of Sulfamoyl Chloride

To a 20 mL round-bottom flask charged with chlorosulfonyl isocyanate (600 μL, 6.85 mmol) under $N_2$ on ice bath, was added formic acid (285.5 μL, 6.85 mmol) dropwise over 5 min with vigorous stirring. After 10 min, the reaction temperature was raised to the room temperature. Within 5 min after warming the reaction mixture to the room temperature, generation of white fog was detected in the flask. After stirring for an hour, the reaction mixture slowly turned into a white solid, which was directly used in the next step without any purification for the next step.

Example 4. Synthetic Procedure for the Preparation of Inhibitor 4

A. 2', 3'-O-isopropylidene Guanosine (8)

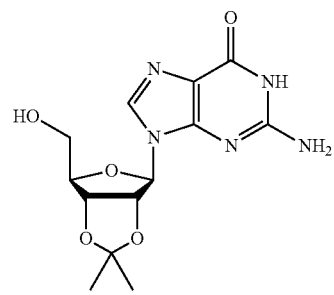

To guanosine (5.01 g, 17.7 mmol) suspended in acetone (300 ml) was added catalytic amount of perchloric acid (1.25 ml) drop-wise while under ice-bath. The reaction mixture suspension became gradually clear and was monitored using TLC (20:80:0.1 MeOH/CHCl$_3$/TEA solvent). At the end of 2 hours, TLC indicated 90% of the product formation. Ammonium hydroxide (2 equivalent to perchloric acid, 2.75 ml) was added drop-wise under ice-bath to neutralize the reaction mixture upon which the product precipitated out from the solution. The reaction mixture was then evaporated under rotary evaporator to complete dryness. The crude reaction mixture was then triturated with ice-cold water (200 ml) overnight. The insoluble material was vacuum-filtered and washed with cold diethyl ether to collect the product (3.99 g, 12.39 mmol) in 70% yield. The $^1$H NMR spectrum was (DMSO-d6): 0.00 (s, TMS internal standard), 1.32 (s, 3H), 1.52 (s, 3H), 3.50-3.56 (m, 2H), 4.10-4.13 (t, 1H), 4.97 (d, 1H), 5.04 (t, 1H), 5.18 (d, 1H), 5.93 (d, 1H), 6.5 (s, 2H), 7.91 (s, 1H) and 10.66 (s, 1H). $^{13}$C-DMSO-d6: 157.16, 154.15, 151.20, 136.30, 117.21, 113.51, 88.87, 87.09, 84.04, 81.64, 62.07, 27.53 and 25.71 ppm. HRMS (ESI+) calcd for $C_{13}H_{18}N_5O_5$ [(M+H)$^+$] 324.1308 found 324.1304.

B. 2',3'-O-isopropylidene-5'-O-(sulfamoyl) guanosine (9)

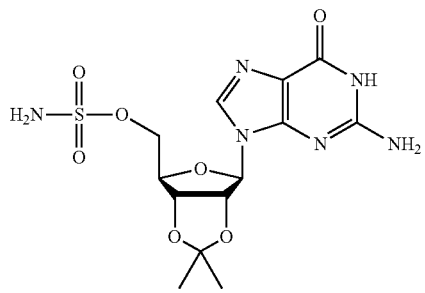

A solution of 8 (0.5 g, 1.54 mmol) in dimethyl acetamide (5 mL) was stirred for 30 min at 0° C. Next, sulfamoyl chloride (1.69 mmol, 194.2 mg) was added to the reaction mixture and stirred for an additional one hour at room temperature. TEA (1.5 mL, excess) was added after an hour and stirring was continued for additional 10 min. The reaction mixture was finally quenched at 0° C. with MeOH (5 ml) and stirred for an additional 15 min. The reaction mixture was evaporated to dryness under reduced pressure. The crude reaction mixture was dissolved in ethyl acetate and washed with saturated NaHCO$_3$ and Brine. The organic layer was collected dried over Na$_2$SO$_4$, filtered and evaporated to dryness. Purification by flash chromatography (20:80:1 MeOH/CH$_2$Cl$_2$/TEA) afforded the title compound (600 mg, 1.49 mmol) in 97% yield (with 1.5 equivalent of TEA). $^1$H NMR spectrum was (DMSO-d6): 1.18 (t, 13.45H), 1.33 (s, 3H), 1.54 (s, 3H), 3.03 (m, 8.86H), 4.13-4.24 (m, 2H), 4.33 (m, 1H), 5.16 (dd, 1H), 5.25 (d, 1H), 5.33 (s, 1H), 6.05 (d, 1H), 6.66 (s, 2H), 7.61 (s, 2H), 7.86 (s, 1H) and 10.84 (s, 1H). $^{13}$C-DMSO-d6: 156.68, 153.74, 150.47, 136.17, 116.75, 113.26, 88.49, 84.02, 83.47, 81.07, 68.30, 51.94, 45.21, 26.84, 25.21, 8.62 and 7.20 ppm. HRMS (ESI+) calcd for C$_{13}$H$_{19}$N$_6$O$_7$S [(M+H)$^+$] 403.1036 found 403.10262.

C. 5'-O—(N-(3-Indole propionic acid) sulfamoyl-2', 3'-O-isopropylidene Guanosine Triethylammonium Salt (10)

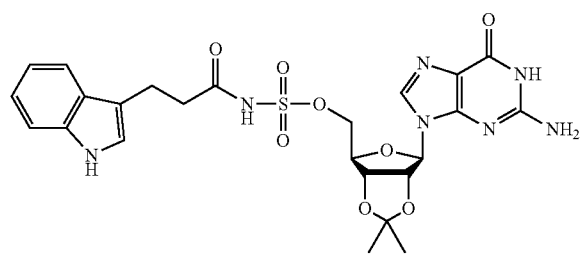

To a stirred solution of 9 (200 mg, 0.5 mmol) and Indole 3-propionic hydroxysuccinimide ester (1.5 equiv, 214 mg, 0.75 mmol) in DMF (2 mL) at 0° C. was added DBU (1.1 equiv, 82 µl, 0.55 mmol). After 10 min at 0° C., the ice bath was removed and the reaction mixture was stirred at rt for overnight. Next, the volatiles were evaporated under reduced pressure and the mixture was directly loaded onto the C18 column. The purification was achieved using a gradient separation (A-ACN, B-1% TEA in water, washed with 2% B and eluted with a gradient of 2-90% of solvent A). Fractions containing the product were combined and evaporated to concentrate. The concentrate was than freezed and lyophilized to obtain 150 mg (0.26 mmol, 51% yield) of the title product as TEA salt (1.0 equivalent of TEA as determined by NMR). $^1$H NMR spectrum was (DMSO-d6): 1.16 (t, 8.61H), 1.30 (s, 3H), 1.51 (s, 3H), 2.37 (t, 2H), 2.85 (t, 2H), 3.17 (m, 6H), 3.93 (m, 1H), 4.09 (m, 1H), 4.27-431 (m, 2H), 5.10 (d, 1H), 5.21 (d, 1H), 5.76 (s, 1H), 5.96 (d, 1H), 6.61 (s, 2H), 6.93 (t, 1H), 7.05 (t, 1H), 7.07 (s, 1H), 7.30 (d, 1H), 7.46 (d, 1H), 7.93 (s, 1H), 10.64 (s, 1H) and 10.64 (s, 1H). $^{13}$C-DMSO-d6: 157.18, 154.19, 151.07, 136.67, 127.64, 122.36, 121.17, 118.68, 118.49, 117.25, 113.40, 111.68, 89.51, 84.43, 83.95, 82.05, 79.65, 55.38, 49.06, 46.23, 27.52, 25.65 and 9.20 ppm. HRMS (ESI+) calcd for C$_{24}$H$_{28}$N$_7$O$_8$S [(M+H)$^+$] 574.1720 found 574.1716.

D. 5'-O—[N-(3-Indole propionic acid)sulfamoyl] Guanosine Triethylammonium Salt (4)

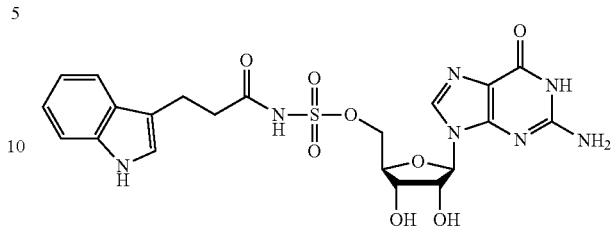

To 10 (25 mg, 0.044 mmol) was added 80% aq TFA (2 ml). After 30 min the reaction mixture was evaporated to dryness (co-evaporated 1% TEA/ethanol for removing TFA) under reduce pressure. The reaction mixture was loaded onto combiflash and purified by reverse phase chromatography using a gradient with solvent (A-ACN. B-Water+0.1% TEA). The peak eluted at 20% of ACN contained the final product. Fractions containing the product were collected and evaporated to get the desired final product in quantitative yields (with 1 equivalent of TEA). $^1$H NMR spectrum was (DMSO-d6): 1.13 (t, 10H), 2.35 (t, 2H), 2.84 (t, 2H), 3.00 (m, 6H), 3.98 (m, 2H), 4.53 (m, 1H), 5.20 (s, 1H), 5.38 (s, 1H), 5.70 (d, 1H), 6.50 (s, 2H), 6.94 (t, 1H), 7.02 (t, 1H), 7.06 (s, 1H), 7.28 (d, 1H), 7.46 (d, 1H), 7.96 (s, 1H), 10.58 (s, 1H) and 10.51 (s, 1H). $^{13}$C-DMSO-d6: 157.22, 154.09, 151.95, 136.66, 136.22, 127.68, 122.39, 121.14, 118.75, 118.47, 117.09, 115.28, 111.66, 86.75, 83.27, 73.79, 71.47, 67.66, 21.94 and 9.47 ppm. HRMS (ESI+) calcd for C$_{21}$H$_{24}$N$_7$O$_8$S [(M+H)$^+$] 534.1407 found 534.1400. The final purity of the compound was ≥99% as indicated by HPLC.

Example 5. Synthetic Procedure for the Preparation of Inhibitor 5

A. 5'-O—(N-(3-butyric acid) sulfamoyl-2', 3'-O-isopropylidene Guanosine Triethylammonium Salt

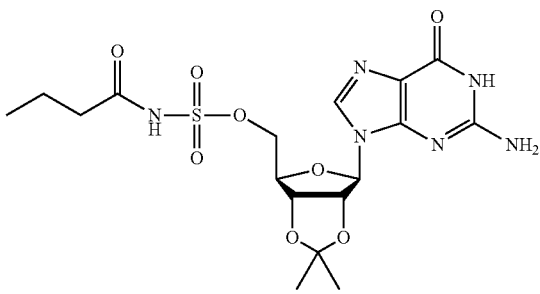

The procedure is similar as described for 10 above using NHS ester (22). The resulting compound was obtained in 60% yield as TEA salt (1.2 equivalent of TEA as determined by NMR). $^1$H NMR spectrum was (DMSO-d6): 0.83 (t, 3H), 1.18 (t, 13H, TEA —CH$_3$), 1.30 (s, 3H), 1.46 (m, 2H), 1.51 (s, 3H), 2.0 (t, 2H), 2.8 (broad, 7H), 3.89 (m, 1H), 4.19 (m, 1H), 4.29 (m, 1H), 5.07 (dd, 1H), 5.19 (dd, 1H), 5.95 (d, 1H), 6.58 (s, 2H), 7.91 (s, 1H) and 10.63 (s, 1H). $^{13}$C-DMSO-d6: 177.93, 156.64, 153.84, 150.78, 136.251, 116.88, 118.49, 113.05, 89.09, 84.12, 83.61, 81.70, 66.78, 41.30, 27.15, 25.27, 19.37 and 14.15 ppm. HRMS (ESI+) calcd for C$_{17}$H$_{25}$N$_6$O$_8$S [(M+H)$^+$] 473.1455 found 473.1450.

B. 5'-O—[N-(3-Butyric acid)sulfamoyl] Guanosine Triethylammonium Salt (5)

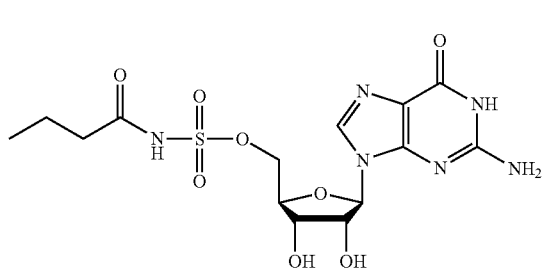

The procedure is similar as described for 4 above. The resulting compound was obtained in 71% yield as TEA salt (1.3 equivalent of TEA as determined by NMR). The final product is highly hygroscopic in nature. $^1$H NMR spectrum was (DMSO-d6): 0.83 (t, 3H), 1.18 (t, 12H), 1.46 (m, 2H), 2.0 (t, 2H), 3.0 (broad, 8H), 4.10-4.15 (m, 2H), 4.48 (m, 1H), 5.24 (dd, 1H), 5.41 (dd, 1H), 5.70 (d, 1H), 6.48 (s, 2H), 7.91 (s, 1H) and 10.61 (s, 1H). $^{13}$C-DMSO-d6: 177.93, 156.64, 153.84, 150.78, 136.251, 116.88, 118.49, 113.05, 89.09, 84.12, 83.61, 81.70, 66.78, 41.30, 27.15, 25.27, 19.37 and 14.15 ppm. HRMS (ESI+) calcd for $C_{14}H_{21}N_6O_8S$ [(M+H)$^+$] 433.1142 found 433.1134.

Example 6. Synthetic Procedure for the Preparation of Inhibitor 7

A. 2', 3'-O-isopropylidene Adenosine (11)

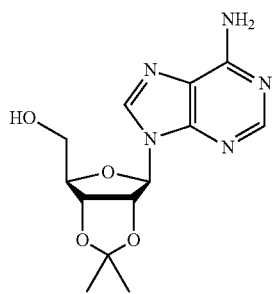

To adenosine (2.02 g, 7.56 mmol) suspended in acetone (150 ml) was added catalytic amount of perchloric acid (0.91 ml) drop-wise while under ice-bath. The milky white reaction mixture turned clear after 2 hours of stirring. The solution was then neutralized using two equivalent of ammonium hydroxide under ice-bath. The reaction mixture was then evaporated to under rotary evaporator to complete dryness and purified using flash silica gel chromatography (gradient: 0% for 4 min, 0-15% for 4-10 min and eluted at 15% MeOH:dichloromethane). The fractions containing the product were evaporated to obtain the product (2.3 g, 3.58 mmol) in 99% yield. The $^1$H NMR spectrum was (DMSO-d6): 1.33 (s, 3H), 1.55 (s, 3H), 3.54-3.56 (m, 2H), 4.22 (m, 1H), 4.97 (dd, 1H), 5.23 (t, 1H), 5.35 (d, 1H), 6.12 (d, 1H), 7.34 (s, 2H), 8.17 (s, 1H) and 8.35 (s, 1H). $^{13}$C-DMSO-d6: 156.60, 153.09, 149.28, 140.16, 119.57, 113.51, 90.07, 86.82, 83.68, 81.82, 62.05, 27.55 and 25.66 ppm. HRMS (ESI+) calcd for $C_{13}H_{18}N_5O_4$ [(M+H)$^+$] 308.1359 found 308.1351.

B. 2', 3'-O-isopropylidene EthenoAdenosine (12)

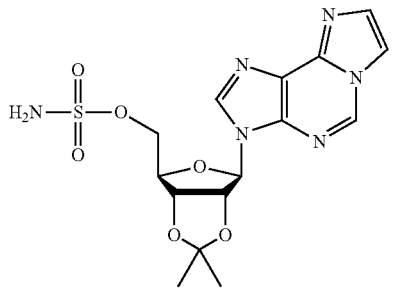

To a stirred solution of 11 (1.1 g, 3.58 mmol) in sodium acetate buffer (100 ml, 0.1M pH 6.5) was added 25 ml of chlorocetaldehyde solution (50% wt) and heated at 40° C. for overnight. Next day, the reaction mixture was cooled down to rt and extracted with EtOAc (2×100 ml). The organic layer was then washed with saturated NaHCO$_3$ and Brine. The organic layer was dried over Na$_2$SO$_4$ and evaporated to dryness under reduced pressure. Purification by flash chromatography (gradient: 0% for 4 min, 0-15% for 4-10 min and eluted at 15:75 MeOH/CH$_2$Cl$_2$) afforded the title compound in 33% (400 mg) yield. The $^1$H NMR spectrum was (DMSO-d6): 1.35 (s, 3H), 1.57 (s, 3H), 3.55-3.56 (m, 2H), 4.12-4.16 (m, 1H), 4.99 (d, 1H), 5.09 (t, 1H), 5.37 (d, 1H), 6.27 (d, 1H), 7.58 (s, 1H), 8.10 (s, 1H), 8.53 (s, 1H) and 9.31 (s, 1H). $^{13}$C-DMSO-d6: 140.90, 140.41, 138.39, 137.65, 133.31, 123.66, 113.61, 112.74, 90.37, 87.27, 84.35, 81.81, 61.92, 27.51, and 25.66 ppm. HRMS (ESI+) calcd for $C_{15}H_{18}N_5O_4$ [(M+H)$^+$] 332.1359 found 332.1350.

C. 2', 3'-O-isopropylidene-5'-O-(sulfamoyl)Etheno-Adenosine (13)

To a 10 ml round-bottom flask containing 12 (100 mg, 0.30 mmol, 1 eq.) in DMF (1 mL), sulfamoyl chloride (103.4 mg, 0.90 mmol, 3 eq.) was added, followed by the slow addition of triethyl amine (40.4 µL, 0.30 mmol, 1.0 eq.) at 0° C. The reaction solution was stirred at r.t. for about 1 hr. DMF was evaporated under high vacuum and the crude reaction mixture was loaded and purified using reverse phase chromatography to obtain (0.27 mmoles, 110 mg) desired product in 90% yield. The $^1$H NMR spectrum was (DMSO-d6): 1.37 (s, 3H), 1.59 (s, 3H), 4.16-4.23 (m, 2H), 4.47 (m, 1H), 5.15 (d, 1H), 5.48 (d, 1H), 6.39 (d, 1H), 7.60 (s, 3H, broad peak overlaid with 1H), 8.13 (s, 1H), 8.50 (s, 1H) and 9.31 (s, 1H). $^{13}$C-DMSO-d6: 140.91, 140.70, 138.18, 137.82, 133.32, 123.90, 114.15, 112.82, 90.08, 84.15, 81.53, 68.44, 46.18, 27.36, and 25.78 ppm. HRMS (ESI+) calcd for $C_{15}H_{19}N_6O_6S$ [(M+H)$^+$] 411.1087 found 411.1076.

D. 2',3'-O-isopropylidene-5'-O—[N-(3-Indolepropionic acid)sulfamoyl]EthenoAdenosine Triethylammonium Salt (10)

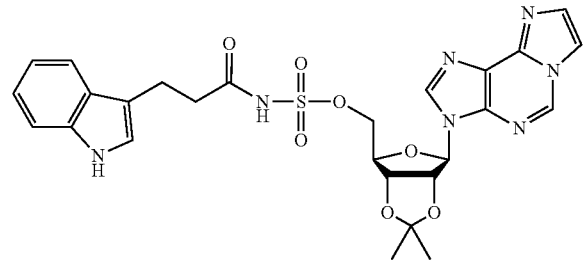

The procedure is similar as described for 6 above using NHS ester (22). The resulting compound was obtained in 55% yield as TEA salt (1.1 equivalent of TEA as determined by NMR). $^1$H NMR spectrum was (DMSO-d6): 1.15 (t, 9H), 1.33 (s, 3H), 1.57 (s, 3H), 2.35 (t, 2H), 2.84 (t, 2H), 3.06 (broad, 6H), 4.04 (d, 2H), 4.45 (m, 1H), 5.07 (m, 1H), 5.39 (m, 1H), 6.30 (d, 1H), 6.95 (m, 1H), 7.02 (m, 1H), 7.06 (s, 1H), 7.29 (d, 1H), 7.46 (d, 1H), 7.56 (d, 1H), 8.08 (s, 1H), 8.59 (s, 1H), 9.30 (s, 1H) and 10.67 (s, 1H). $^{13}$C-DMSO-d6: 140.93, 140.44, 138.47, 137.67, 136.68, 133.29, 127.66, 123.47, 122.36, 121.15, 118.71, 118.45, 113.63, 112.71, 111.67, 90.37, 84.57, 84.34, 82.10, 27.52, 25.62, 21.93 and 9.28 ppm. HRMS (ESI+) calcd for $C_{26}H_{28}N_7O_7S$ [(M+H)$^+$] 582.1771 found 582.1764.

E. 5'-O—[N-(3-Indole propionic acid)sulfamoyl]EthenoAdenosine Triethylammonium Salt (7)

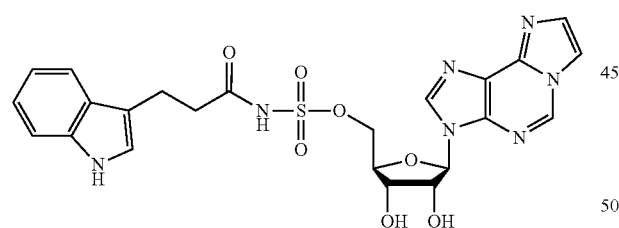

The procedure is similar as described for 2a above. The resulting compound was obtained in 74% yield as TEA salt (1.3 equivalent of TEA as determined by NMR). The final product is highly hygroscopic in nature. $^1$H NMR spectrum was (DMSO-d6): 1.10 (t, 13H), 2.37 (t, 2H), 2.87 (t, 2H), 2.91 (broad, 6H), 4.04 (d, 2H), 4.67 (m, 1H), 5.37 (m, 1H), 5.53 (m, 1H), 6.07 (d, 1H), 6.94 (m, 1H), 7.03 (m, 1H), 7.08 (s, 1H), 7.29 (d, 1H), 7.48 (d, 1H), 7.56 (d, 1H), 8.07 (s, 1H), 8.62 (s, 1H), 9.29 (s, 1H) and 10.67 (s, 1H). $^{13}$C-DMSO-d6: 141.01, 140.37, 139.11, 137.51, 136.66, 133.21, 127.68, 122.39, 121.14, 118.75, 118.46, 115.30, 112.62, 111.65, 87.86, 83.66, 74.61, 71.48, 46.22 and 21.93 ppm. HRMS (ESI+) calcd for $C_{23}H_{24}N_7O_7S$ [(M+H)$^+$] 542.1458 found 542.1457. The final purity of the compound was ≥99% as indicated by HPLC.

Example 7. Synthetic Procedure for the Preparation of Inhibitor 6

A. N,N-Dimethylaminomethylene-2',3'-O,O-isopropylideneguanosine (14)

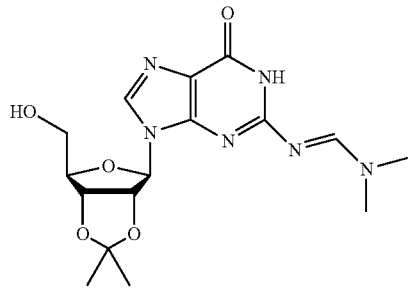

To a suspension of 4 (0.575 g, 1.78 mmol) in DMF (6 mL), N,N-dimethylformamide dimethyl acetal (0.891 mL, 6.7 mmol) was added under argon to yield an orange-brown solution. The reaction mixture was stirred at 50° C. for 4 h. The solvent was removed under reduced pressure and at elevated temperatures; the white residue was then removed by filtration. The filtrate was dried under reduced pressure, redissolved in MeOH (2.5 mL) and precipitated with 5 mL of EtOAc. After storage overnight at 4° C., the residue was removed by filtration and the combined filtrates were thoroughly washed with EtOAc and dried under reduced pressure. The product was obtained as a white powder in 80% yield (0.538 g, 1.42 mmol). The $^1$H NMR spectrum was (DMSO-d6): 1.33 (s, 3H), 1.55 (s, 3H), 3.04 (s, 3H), 3.16 (s, 3H), 3.51-3.55 (m, 2H), 4.12-4.15 (m, 1H), 4.97 (dd, 1H), 5.05 (t, 1H), 5.28 (d, 1H), 6.04 (d, 1H), 8.02 (s, 1H), 8.57 (s, 1H) and 11.37 (s, 1H). $^{13}$C-DMSO-d6: 158.7, 158.03, 157.86, 149.92, 137.64, 120.24, 113.58, 88.97, 86.74, 83.93, 81.57, 61.87, 41.22, 35.12, 27.54 and 25.71 ppm. HRMS (ESI+) calcd for $C_{16}H_{23}N_6O_5$ [(M+H)$^+$] 379.1730 found 379.1738.

B. N,N-Dimethylaminomethylene-2',3'-O,O-isopropylidene-5'-deoxy-5'-azido Guanosine (12b)

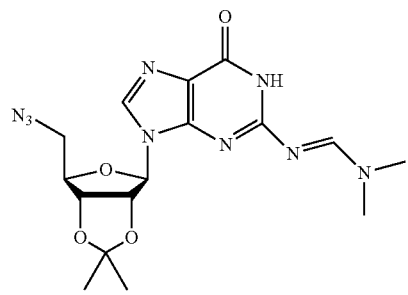

A suspension of 14 (0.440 g, 1.162 mmol) in anhyd THF (22 mL) under argon was cooled to −70° C. by a mixture of dry ice and acetone. Methyltriphenoxyphosphonium iodide (0.788 g, 1.742 mmol; 1.5 equiv) was added. Due to the light sensitivity of the reactant and the product all subsequent steps were carried out under exclusion of light. After 30 min of stirring the reaction mixture was allowed to warm to r.t. and stirred for another 4 h. The reaction was stopped by the addition of MeOH (10 mL) and the solvent was removed under reduced pressure. The dark red residue was dissolved in MeOH/CHCl₃ (1:4; 2.5 mL) and CHCl₃ (14 mL) was added. The solution of the crude product was subjected to chromatography on silica gel (Combiflash: CHCl₂/MeOH, 9:1). After removal of the solvent, the 5'-iodo product 12a was obtained as a yellow-orange solid in 92% yield (0.522 g, 1.15 mmol). The ¹H NMR spectrum was (DMSO-d6): 1.35 (s, 3H), 1.56 (s, 3H), 3.06 (s, 3H), 3.19 (s, 3H), 3.54-3.58 (m, 2H), 4.264 (m, 1H), 5.0 (dd, 1H), 5.43 (dd, 1H), 5.05 (t, 1H), 6.12 (d, 1H), 8.04 (s, 1H), 8.61 (s, 1H) and 11.43 (s, 1H). ¹³C-DMSO-d6: 158.59, 158.02, 157.85, 149.84, 137.82, 120.41, 114.04, 88.78, 84.78, 83.67, 81.70, 60.23, 41.68, 35.14, 27.43 and 25.70 ppm. HRMS (ESI+) calcd for $C_{16}H_{22}IN_6O_4$ [(M+H)⁺] 489.0747 found 489.0736.

To a solution of (12a) (400 mg, 0.8 mmol) in dry DMF (5 ml) was added sodium azide (260 mg, 8 mmol) and stirred under argon at RT overnight. After 12 hrs the reaction mixture was filtered and washed with cold methanol. The filtrate was evaporated to dryness and the final product was purified using flash chromatography. The desired peak was eluted at 10% MeOH/CHCl₃ mixture, which was combined and evaporated to obtain 166 mg of the azido product 12b in 55% yield. The ¹H NMR spectrum was (DMSO-d6): 1.36 (s, 3H), 1.55 (s, 3H), 3.06 (s, 3H), 3.19 (s, 3H), 3.55-3.58 (m, 2H), 4.26 (m, 1H), 4.99 (dd, 1H), 5.42 (d, 1H), 6.16 (d, 1H), 8.04 (s, 1H), 8.60 (s, 1H) and 11.37 (s, 1H). ¹³C-DMSO-d6: 158.55, 157.97, 157.78, 149.52, 138.21, 120.42, 113.81, 89.70, 86.68, 84.30, 84.23, 60.23, 41.68, 35.21, 27.31, and 25.64 ppm. HRMS (ESI+) calcd for $C_{16}H_{23}N_6O_5$ [(M+H)⁺] 404.1795 found 404.1786.

C. N,N-Dimethylaminomethylene-2',3'-O,O-isopropylidene-5'-deoxy-5'-amino Guanosine (15)

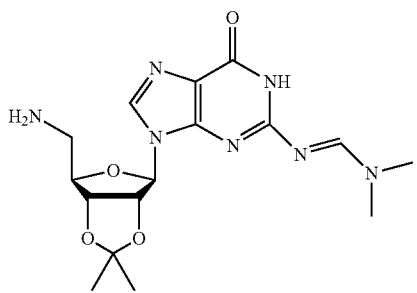

A solution of 12b (160 mg, 0.392 mmol) in dioxane (12 mL) was added H₂O (1.6 mL), TEA (65.6 uL, 0.464 mmol) and triphenylphosphine (0.312 g, 1.18 mmol). The reaction was maintained in an oil bath at 50° C. for 3 hrs. The reaction was cooled, concentrated, and the residue was purified using flash silica column chromatography, then eluted using a gradient of 20% CH₃OH (containing 0.5% TEA) to chloroform in 20 min. The product 15 eluted as a broad peak, which was concentrated to give product (80 mg, 0.212 mmol) in 54% yield. The ¹H NMR spectrum was (DMSO-d6): 0.95 (s, 1H), 1.33 (s, 3H), 1.54 (s, 3H), 2.75 (m, 2H), 3.04 (s, 3H), 3.19 (s, 3H), 4.08 (m, 1H), 4.98 (dd, 1H), 5.34 (d, 1H), 5.99 (d, 1H), 8.03 (s, 1H) and 8.56 (s, 1H). ¹³C-DMSO-d6: 158.63, 158.04, 157.81, 149.95, 137.98, 120.46, 113.66, 89.94, 86.68, 83.38, 81.85, 46.18, 43.82, 35.14, 27.56, 25.78 and 11.91 ppm. HRMS (ESI+) calcd for $C_{16}H_{24}N_7O_4$ [(M+H)⁺] 378.1890 found 378.1885.

D. N,N-Dimethylaminomethylene-2',3'-O,O-isopropylidene-5'-deoxy-5'-N-Sulfamoyl Guanosine (17)

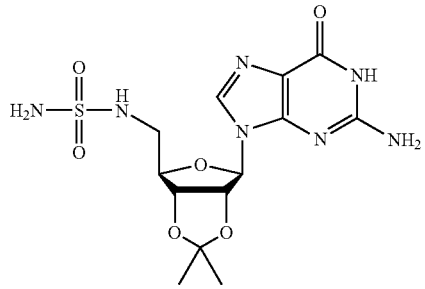

To a solution of 15 (0.150 g, 0.31 mmol) in 1,4-dioxane (8 ml) was added sulfamide (0.090 g, 0.93 mmol) and the mixture was refluxed for 2 hours. The reaction mixture was evaporated and redissolved in CH₂Cl₂ (15 ml) and water (15 ml). The organic layer was collected, washed with brine, dried (Na₂SO₄) and evaporated to dryness under reduced pressure to obtain the crude 5'-N-sulfomylated product. To a solution of 5'-N-sulfomylated product 16 dissolved in MeOH (5 ml) was added 4N NaOH (5 ml). The reaction mixture solution was heated at 60° C. for 140 hrs, cooled in an ice bath and neutralize with 1N HCl. The organic was evaporated and the aqueous solution was lyophilized to obtain crude product 17. The crude was loaded and purified using reverse phase chromatography to obtain the product (0.030 g, 0.074 mmol) in 24% yields over two steps. ¹H NMR spectrum was (DMSO-d6): 0.941 (t, 1H), 1.36 (s, 3H), 1.54 (s, 3H), 3.12-3.33 (m, 2H), 4.28 (m, 1H), 5.02 (dd, 1H), 5.22 (dd, 1H), 5.93 (d, 1H), 6.60 (s, 2H), 6.72 (s, 2H), 6.96 (s, 1H), 7.86 (s, 1H) and 10.76 (s, 1H). ¹³C-DMSO-d6: 157.40, 154.41, 150.71, 137.09, 117.90, 113.70, 89.65, 84.38, 83.05, 82.19, 46.18, 43.82, 27.56, 25.76 and 12.24 ppm. HRMS (ESI+) calcd for $C_{13}H_{20}N_7O_6S$ [(M+H)⁺] 402.1196 found 402.1193.

E. 5'-N—[N-(3-Indole propionic acid)sulfamoyl] Guanosine Triethylammonium Salt (6)

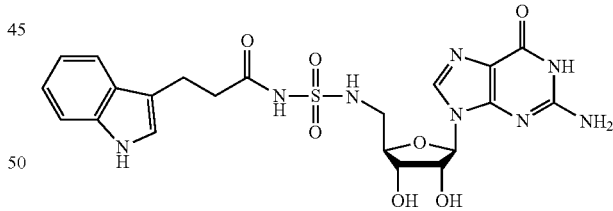

To a stirred solution of 17 (20 mg, 0.05 mmol) and Indole 3-propionic hydroxysuccinimide ester (1.5 equiv, 21.4 mg, 0.075 mmol) in DMF (0.4 mL) at 0° C. was added DBU (1.1 equiv, 8.2 µl, 0.055 mmol). After 10 min at 0° C., the ice bath was removed and the reaction mixture was stirred at r.t. for overnight. Next, the volatiles were evaporated under reduced pressure and the crude reaction mixture was used for further final step without purification. To the crude reaction mixture was added 80% aq TFA (1 ml). After 30 min the reaction mixture was evaporated to dryness (co-evaporated 1% TEA/ethanol for removing TFA) under reduce pressure. The reaction mixture was loaded onto combiflash and purified by reverse phase chromatography using a gradient with solvent (A-ACN, B-Water+0.1% TEA). The peak eluted at 20% of ACN contained the final product. Fractions containing the product were collected and evaporated to get the desired final product in quantitative yields (with 1 equivalent of TEA). $^1$H NMR spectrum was 700 MHz (DMSO-d6): 0.95 (t, 9H), 2.73 (m, 6H), 2.87-2.97 (m, 4H), 3.87-3.92 (m, 2H), 4.11 (m, 1H), 4.41-4.50 (m, 3H), 5.51 (d, 1H), 5.57 (d, 1H), 6.85-6.95 (m, 4H), 7.39-7.41 (m, 2H), 7.69-7.74 (m, 2H), and 10.72 (d, 2H). $^{13}$C-DMSO-d6: 157.58, 156.42, 154.12, 151.15, 136.83, 128.76, 128.10, 127.44, 123.16, 121.19, 118.39, 111.64, 91.22, 88.26, 80.68, 78.38, 72.61, 66.19, 53.68, 52.36, 46.27, 21.94 and 10.21 ppm. HRMS (ESI+) calcd for $C_{21}H_{25}N_8O_7S$ $[(M+H)^+]$ 533.1567 found 533.1567. The final purity of the compound was ≥99% as indicated by HPLC.

Example 8. Evaluation of Compound 7

The interactions between the mu-opioid (MOR) and N-methyl-D-aspartate (NMDAR) receptors are an area of intense investigation due to their contribution to maladaptive neuroplasticity. Recent evidence suggests that their association requires the involvement of histidine triad nucleotide binding protein (HINT1). Since it is known that spinal blockade of NMDA receptors prevents the development of opioid analgesic tolerance, it was hypothesized that spinal inhibition of the HINT1 enzyme may similarly inhibit opioid tolerance. Given the similar mechanisms underlying the development of both opioid analgesic tolerance and neuropathic pain, we reasoned that HINT1 inhibition may reduce the development of neuropathic pain, consistent with prior observations that antagonism of NMDA receptors inhibits both developments. Blockade of NMDA receptors is known to inhibit the development of MOR analgesic tolerance. To address these questions HINT1 inhibitors were evaluated in three models of spinal neuroplasticity: morphine-induced inhibition of NMDA-evoked behavior, endomorphin-2 induced analgesic tolerance, and spared nerve injury.

A. Inhibition of Morphine Inhibition of NMDA-Evoked Behavior (FIGS. 2A-C).

Male ICR mice (25-30) were given TpGc (10 nmol) 10 minutes before morphine sulfate (10 nmol) intrathecally. After a period of 10 minutes, NMDA was injected intrathecally and scratching and biting behaviors were quantified. The MPE % was calculated using morphine alone as the positive control.

Figure 2A:
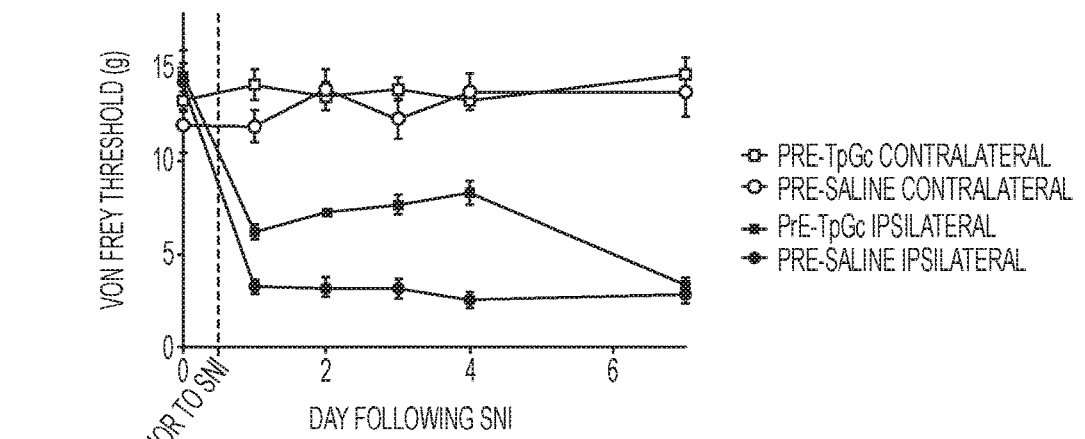
FIGS. 2A-C are plots of the von Frey threshold and the day following spared never injury (SNI) as a function of HINT1 inhibitor, where references to "3A" are references to compound 7, disclosed herein.
Figure 2B:
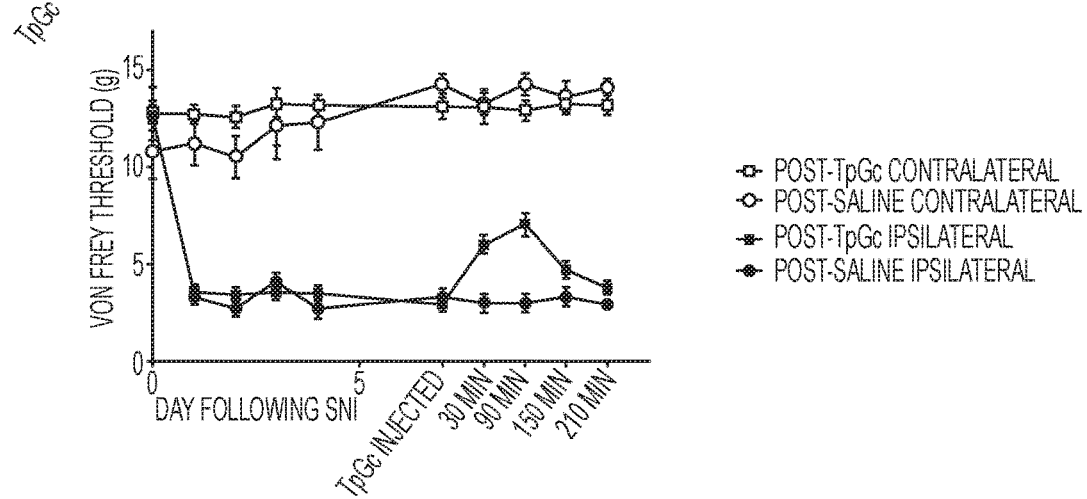
Figure 2C:
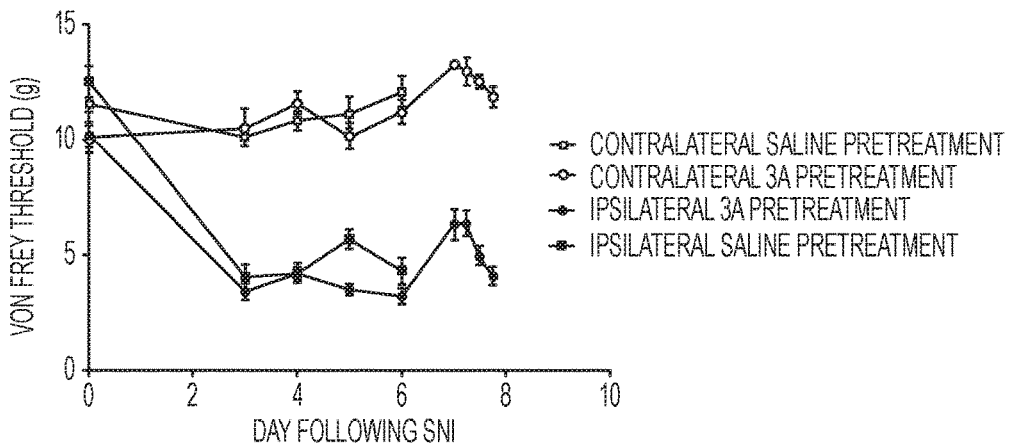

The results shown in FIGS. 2A-C show that HINT1 inhibition attenuates or reverses the development of chronic pain behaviors. Male and Female ICR mice (25-30 g) were given 1 nmol of TpGc prior to (Panel A) or 7 days post (Panel B) spared nerve injury. A separate cohort (Panel C) of male ICR mice (25-50 g) were given 1 nmol of compound 7 intrathecally both prior to and 7 days post spared nerve injury. All cohorts were evaluated with Von Frey mechanical threshold testing. Pretreatment with TpGc led to a sustained attenuation of SNI-induced mechanical hypersensitivity. Injection of TpGc on day 7 following injury led to a transient reversal of mechanical hypersensitivity. Pretreatment with TpGc3a (Panel C) did not lead to an attenuation of pain behavior, however injection of 1 nmol of compound 7 on day 7 following injury did lead to a transient reversal that resolved at 4 hours post injection.

B. Inhibition of Opioid Tolerance

Male ICR mice (25-30 g) were given seven (7) intrathecal injections of either saline, morphine, HINT1 inhibitor, or HINT1 inhibitor+morphine over the course of 3 days. A final probe dose of intrathecal morphine was give and mice were behaviorally assessed via a tail flick assay. The maximum possible effect was calculated ((postdrug latency-predrug latency)/(cutoff-predrug latency)) and $ED_{50}$ values were calculated by parametric linear regression analysis of the log dose-response curves according to Tallarida and Murray, 1987.

The results showed that TpGc and analogs inhibit morphine's ability to inhibit NMDA-evoked behaviors. Male mice were given intrathecal treatment of either morphine or morphine+a HINT1 inhibitor. They were then given an intrathecal injection of NMDA and scratching and biting behaviors were counted for 1 minute. Pretreatment with either TpGc ($ED_{50}$=0.61 nM (0.28, 1.4)) or compound 7 ($ED_{50}$=0.47 nM (0.20, 1.1)) attenuated morphine's inhibition of NMDA-evoked behavior. Other compounds that were tested include:

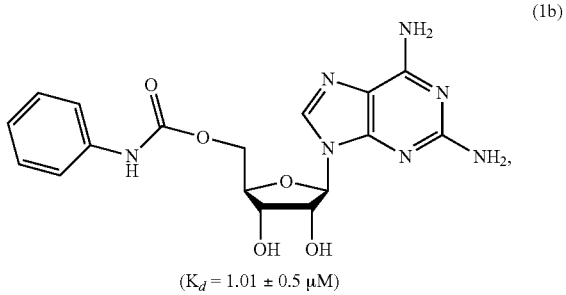

(1b)

($K_d$ = 1.01 ± 0.5 µM)

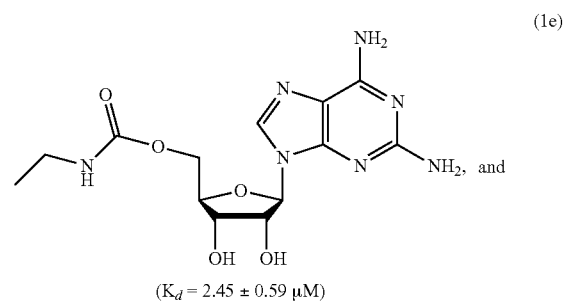

(1e)

($K_d$ = 2.45 ± 0.59 µM)

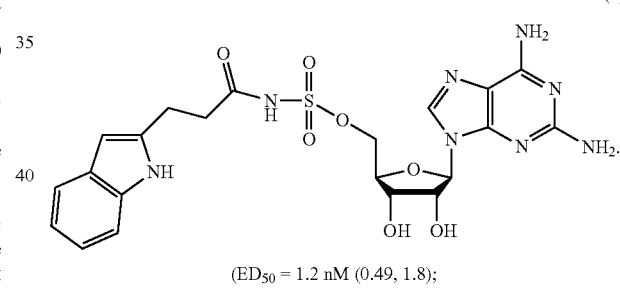

(4)

($ED_{50}$ = 1.2 nM (0.49, 1.8);
$K_d$ = 0.81 ± 0.11 µM).
Compounds 1b and 1e are soluble in DMSO.

C. Neuropathic Pain (FIGS. 3A-B)

Male and female ICR mice were given 1 nmol of HINT1 inhibitor TpGc or 7 intrathecally either immediately prior to or 7 days following induction of neuropathic pain via spared nerve injury (Decosterd, 2000). Briefly, an incision is made into the leg of the mouse directly above the branching of the sciatic nerve. The peroneal and tibial branches of the nerve are ligated and cut while the sural branch is left intact, leading to a localized hypersensitivity on the lateral portion of the hindpaw. Von Frey mechanical testing was performed prior to surgery and for up to 7 days post surgery.

Figure 3A:
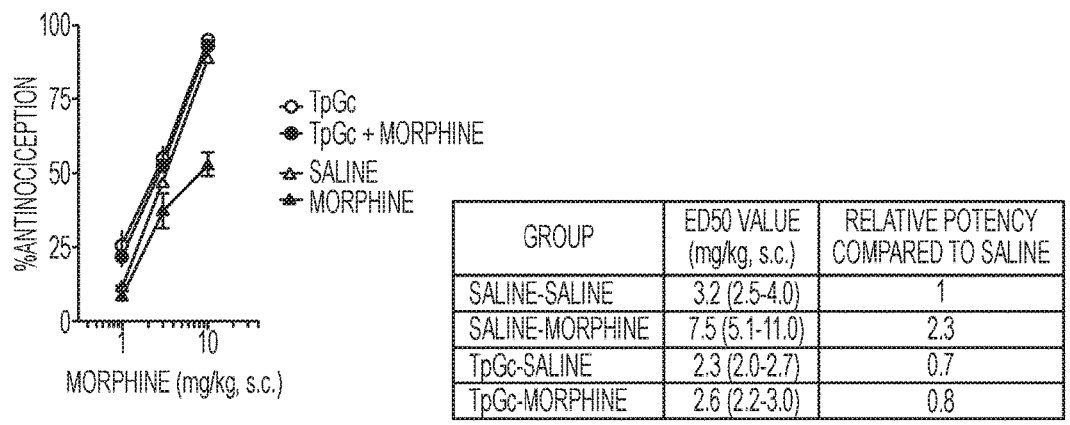
FIGS. 3A-B are plots of percent antinociception and morphine (mg/kg, s.c.) as a function of HINT1 inhibitor, where references to "3A" are references to compound 7, disclosed herein.
Figure 3B:
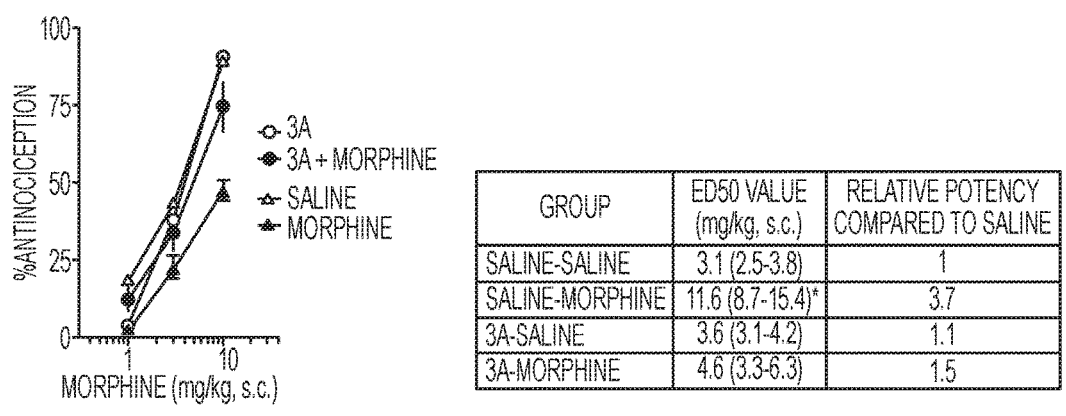
Figure 4:
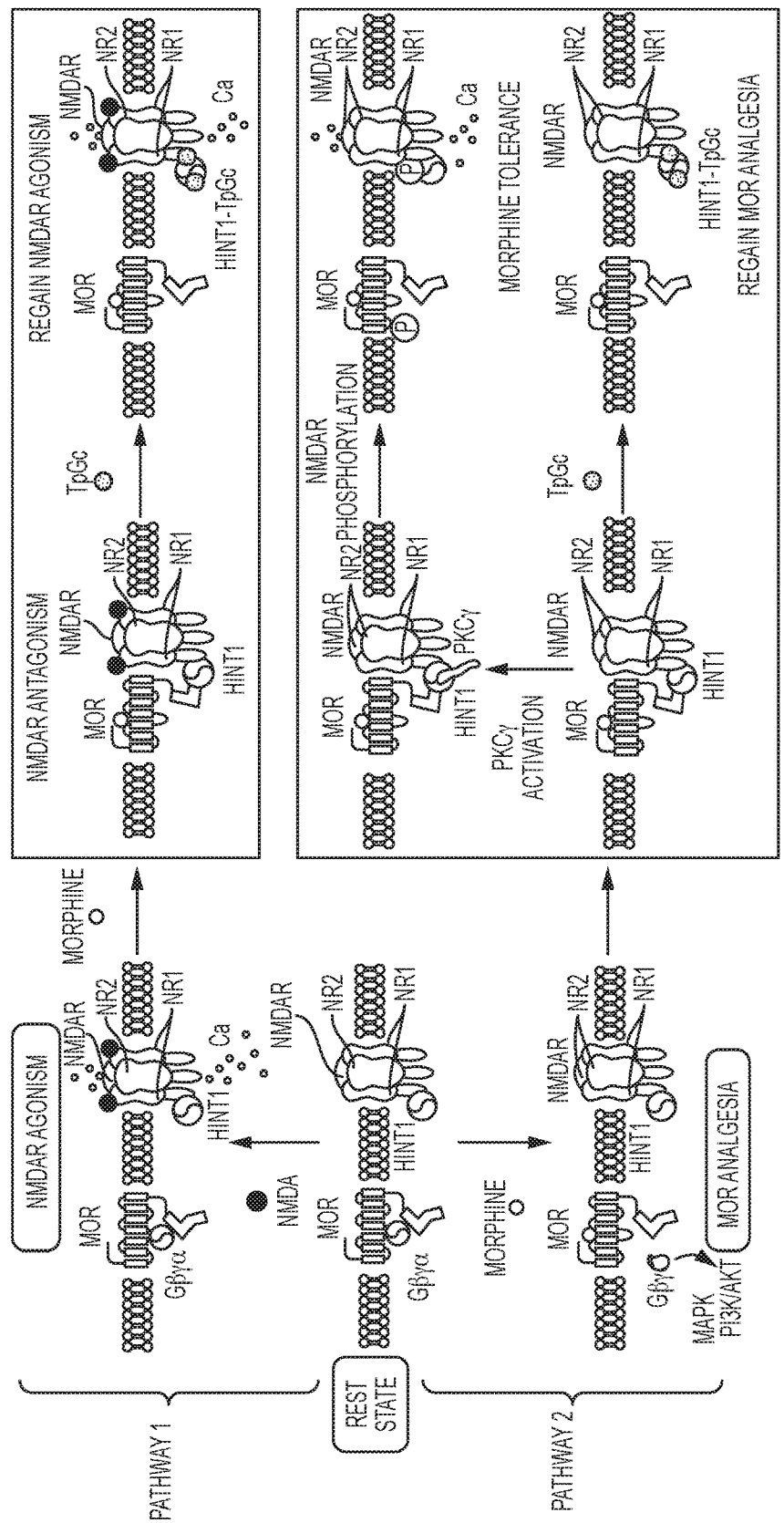
FIG. 4 is a schematic of a proposed mechanism of action for compounds described herein.

The results shown in FIGS. 3A-B show the effects of HINT1 inhibitors TpGc or compound 7 on development of morphine tolerance. Subjects underwent a tolerance development protocol where they were pre-treated with either saline, morphine, HINT1 inhibitor, or HINT1 inhibitor+morphine intrathecally for 3 days. Analgesic dose-response curves were generated following acute intrathecal morphine challenge on Day 4. Subjects treated with morphine displayed decreased morphine potency and efficacy, indicating the induction of chronic morphine analgesic tolerance. However, pretreatment with HINT1 inhibitors displayed equivalent potency and efficacy compared to the saline pre-treatment, indicating a lack of opioid tolerance.

These studies indicate to that disruption of HINT1 via enzymatic inhibitors TpGc and compound 7 is a viable strategy to target maladaptive plasticity involving MOR and NMDA-mediated signaling. Delivery of TpGc and TpGc3a attenuate the development of opioid tolerance, attenuate or reverse chronic pain behaviors (FIGS. 3A-B) and interrupts morphine's inhibition of NMDA-evoked scratching and biting behaviors (FIGS. 2A-C). These results elucidate the interaction of MOR and NMDAR interaction at the level of the spinal cord.

Example 9. Additional Compounds

Additional compounds contemplated herein include compounds of the formula:

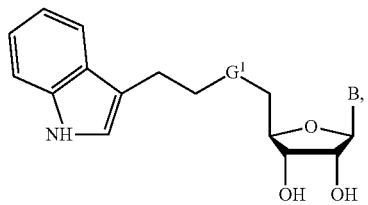

wherein:
B is:

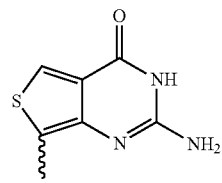

and $G^1$ is —C(O)NHSO$_2$O— (2b); and B is:

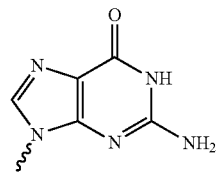

and $G^1$ is —NH—P(O)(OH)S— (2c). Compound 2b has a $K_d$ (μM) of 5.2. Compounds 2b and 2c are both highly water soluble.

Still other compounds contemplated herein include compounds of the formula:

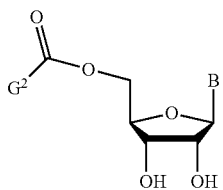

wherein:
$G^2$ is tryptamine (1a), histamine (1c), benzylamine (1d) or diethylamine (1f); and
B is

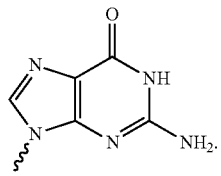

Compounds 1a, 1c, 1d, and 1f have a $K_d$ (μM) of 3.65±1.0; 3.43±0.7; 8.09±0.09; and 47.18±1.5, respectively. Compounds 1a, 1c, 1d, and 1f are soluble in DMSO; DMSO; insoluble; and DMSO, respectively.

Yet other compounds contemplated herein include compounds of the formula:

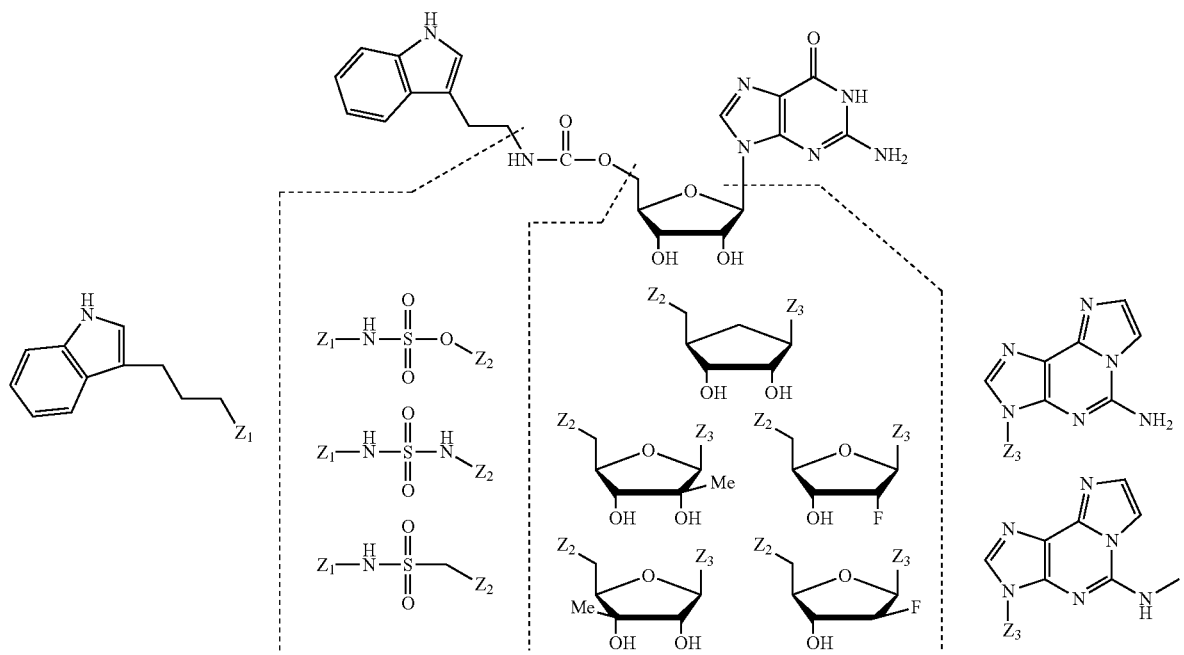

-continued

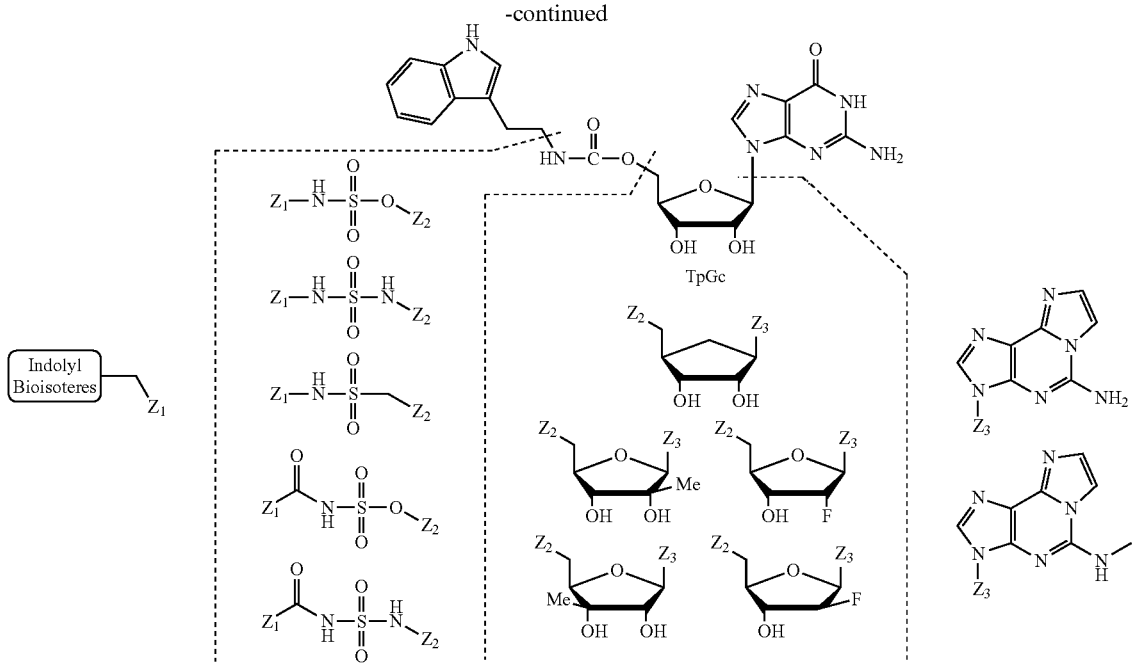

wherein suitable indolyl isosteres include, but are not limited to, those described in M. Redlich, "Indoles and Indole Isosteres," *Chemfiles* 10: Article 2 (http://www.sigmaaldrich.com/technical-documents/articles/chemfiles/indoles-and-indole.html); http://www.sigmaaldrich.com/chemistry/chemical-synthesis/technology-spotlights/indoles.html (accessed on 9 Aug. 2017); and L. Lima and E. Barreiro, *Current Medicinal Chemistry* 12: 23-49 (2005), all of which are incorporated by reference as if fully set forth herein.

Still other compounds contemplated herein include compounds of the formulae:

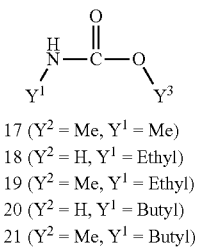

17 ($Y^2$ = Me, $Y^1$ = Me)
18 ($Y^2$ = H, $Y^1$ = Ethyl)
19 ($Y^2$ = Me, $Y^1$ = Ethyl)
20 ($Y^2$ = H, $Y^1$ = Butyl)
21 ($Y^2$ = Me, $Y^1$ = Butyl)

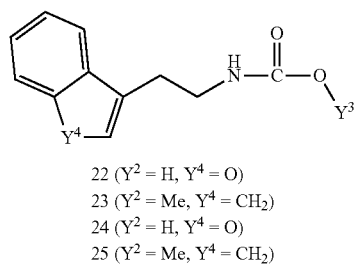

22 ($Y^2$ = H, $Y^4$ = O)
23 ($Y^2$ = Me, $Y^4$ = CH$_2$)
24 ($Y^2$ = H, $Y^4$ = O)
25 ($Y^2$ = Me, $Y^4$ = CH$_2$)

-continued 26 ($Y^2$ = H, $Y^4$ = NH)
27 ($Y^2$ = Me, $Y^4$ = CH$_2$)
28 ($Y^2$ = H, $Y^4$ = NH)
29 ($Y^2$ = Me, $Y^4$ = CH$_2$)

wherein $Y^3$ is:

Yet other compounds contemplated herein include compounds of the formulae:

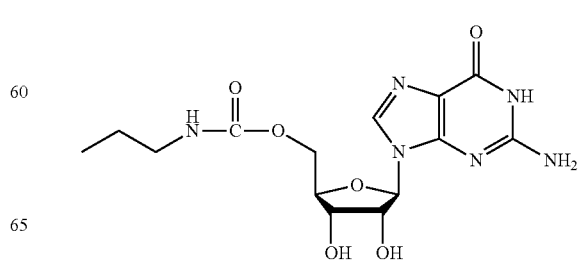

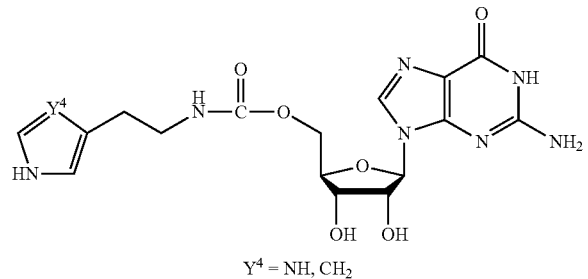

Y⁴ = NH, CH₂

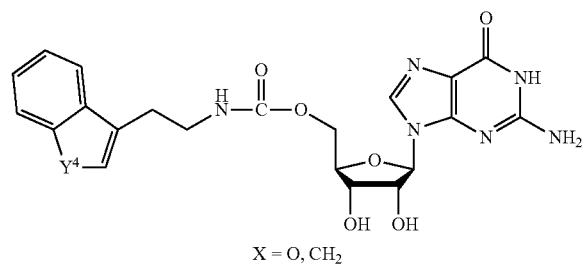

X = O, CH₂

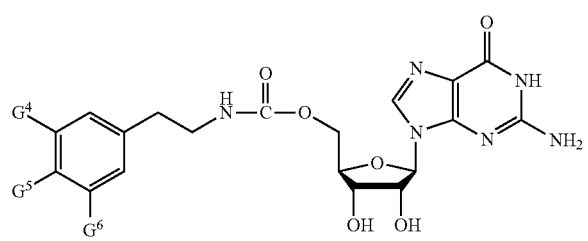

a G⁶ = F, G⁴ = H, G⁵ = H
b G⁶ = Cl, G⁴ = H, G⁵ = H
c G⁶ = CF₃, G⁴ = H, G⁵ = H
d G⁶ = H, G⁴ = OCH₃, G⁵ = OCH₃

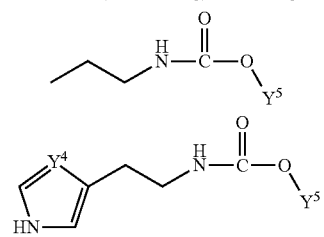

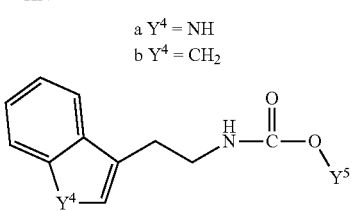

a Y⁴ = NH
b Y⁴ = CH₂

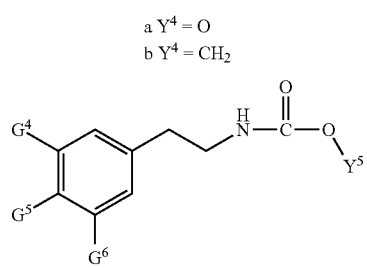

a Y⁴ = O
b Y⁴ = CH₂

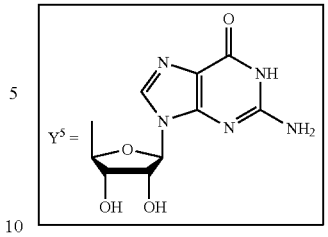

a G⁶ = F, G⁴ = H, G⁵ = H
b G⁶ = Cl, G⁴ = H, G⁵ = H
c G⁶ = CF₃, G⁴ = H, G⁵ = H
d G⁶ = H, G⁴ = OCH₃, G⁵ = OCH₃

The patents, patent documents and other publications cited herein, are incorporated by reference herein as though fully set forth.

1. Liu, Q.; Puche, A. C.; Wang, J. B. Distribution and expression of protein kinase C interactive protein (PKCI/HINT1) in mouse central nervous system (CNS). *Neurochem. Res.* 2008, 33, 1263-1276.
2. Garzón, J.; Herrero-Labrador, R.; Rodríguez-Muñoz, M.; Shah, R.; Vicente-Sánchez, A.; Wagner, C. R.; Sánchez-Blázquez, P. HINT1 protein: a new therapeutic target to enhance opioid anti-nociception and block mechanical allodynia. *Neuropharmacology* 2015, 89, 412-423.
3. Chou, T. F.; Baraniak, J.; Kaczmarek, R.; Zhou, X.; Cheng, J.; Ghosh, B.; Wagner, C. R. Phosphoramidate pronucleotides: a comparison of the phosphoramidase substrate specificity of human and *Escherichia coli* histidine triad nucleotide binding proteins. *Mol Pharm.* 2007, 4, 208-217.
4. Wang, J.; Fang, P.; Schimmel, P.; Guo, M. Side chain independent recognition of aminoacyl adenylates by the Hint1 transcription suppressor. *J Phys Chem. B.* 2012, 116, 6198-6805.
5. Zhou, X.; Chou, T. F.; Aubol, B. E.; Park, C. J.; Wolfenden, R.; Adams, J.; Wagner, C. R. Kinetic mechanism of human histidine triad nucleotide binding protein 1. *Biochemistry* 2013, 52, 3588-3600.
6. Lima, C. D.; Klein, M. G.; Hendrickson, W. A. Structure-based analysis of catalysis and substrate definition in the HIT protein family. *Science* 1997, 278, 286-290.
7. Murakami, E.; Tolstykh, T.; Bao, H.; Niu, C.; Steuer, H. M.; Bao, D.; Chang, W.; Espiritu, C.; Bansal, S.; Lam, A. M.; Otto, M. J.; Sofia, M. J.; Furman, P. A. Mechanism of activation of PSI-7851 and its diastereoisomer PSI-7977. *J Biol Chem.* 2010, 285, 34337-34347.
8. Drontle, D. P.; Wagner, C. R. Designing a pronucleotide stratagem: lessons from amino acid phosphoramidates of anticancer and antiviral pyrimidines. *Mini Rev Med Chem.* 2004, 4, 409-419.
9. Li, S.; Jia, Y.; Jacobson, B.; McCauley, J.; Kratzke, R.; Bitterman, P. B.; Wagner, C. R. Treatment of breast and lung cancer cells with a N-7 benzyl guanosine monophosphate tryptamine phosphoramidate pronucleotide (4Ei-1) results in chemosensitization to gemcitabine and induced eIF4E proteasomal degradation. *Mol Pharm.* 2013, 10, 523-531.
10. Abraham, T. W.; Kalman, T. I.; McIntee, E. J.; Wagner, C. R. Synthesis and biological activity of aromatic amino acid phosphoramidates of 5-fluoro-2'-deoxyuridine and 1-beta-arabinofuranosylcytosine: evidence of phosphoramidase activity. *J Med Chem.* 1996, 39, 4569-4575.
11. Chou, T. F.; Wagner, C. R. Lysyl-tRNA synthetase-generated lysyl-adenylate is a substrate for histidine triad nucleotide binding proteins. *J Biol Chem.* 2007, 282, 4719-4727.

12. Lee, Y. N.; Nechushtan, H.; Figov, N.; Razin, E. The function of lysyl-tRNA synthetase and Ap4A as signaling regulators of MITF activity in FcepsilonRI-activated mast cells. *Immunity* 2004, 20, 145-151.
13. Li, H.; Zhang, Y.; Su, T.; Santella, R. M.; Weinstein, I. B. Hint1 is a haplo-insufficient tumor suppressor in mice. *Oncogene* 2006, 25, 713-721.
14. Wang, L.; Zhang, Y.; Li, H.; Xu, Z.; Santella, R. M.; Weinstein, I. B. Hint1 inhibits growth and activator protein-1 activity in human colon cancer cells. *Cancer Res.* 2007, 67, 4700-4708.
15. Varadarajulu, J.; Schmitt, A.; Falkai, P.; Alsaif, M.; Turck, C. W.; Martins-de-Souza, D. Differential expression of HINT1 in schizophrenia brain tissue. *Eur Arch Psychiatry Clin Neurosci.* 2012, 262, 167-172.
16. Barbier, E.; Zapata, A.; Oh, E.; Liu, Q.; Zhu, F.; Undie, A.; Shippenberg, T.; Wang, J. B. Supersensitivity to amphetamine in protein kinase-C interacting protein/HINT1 knockout mice. *Neuropsychopharmacology* 2007, 32, 1774-1782.
17. Jackson, K. J.; Wang, J. B.; Barbier, E.; Damaj, M. I.; Chen, X. The histidine triad nucleotide binding 1 protein is involved in nicotine reward and physical nicotine withdrawal in mice. *Neurosci Lett.* 2013, 550, 129-133.
18. Rodríguez-Muñoz, M.; Sánchez-Blázquez, P.; Vicente-Sánchez, A.; Bailón, C.; Martín-Aznar, B.; Garzón, J. The histidine triad nucleotide-binding protein 1 supports mu-opioid receptor-glutamate NMDA receptor cross-regulation. *Cell Mol Life Sci.* 2011, 68, 2933-2949.
19. Guang, W.; Wang, H.; Su, T.; Weinstein, I. B.; Wang, J. B. Role of mPKCI, a novel mu-opioid receptor interactive protein, in receptor desensitization, phosphorylation, and morphine-induced analgesia. *Mol Pharmacol.* 2004, 66, 1285-1292.
20. Kawasumi, M.; Nghiem, P. Chemical genetics: elucidating biological systems with small-molecule compounds. *J Invest Dermatol.* 2007, 127, 1577-1584.
21. Duckworth, B. P.; Geders, T. W.; Tiwari, D.; Boshoff, H. I.; Sibbald, P. A.; Barry, C. E.: Schnappinger, D.; Finzel, B. C.; Aldrich, C. C. Bisubstrate adenylation inhibitors of biotin protein ligase from *Mycobacterium tuberculosis*. *Chem Biol.* 2011, 18, 1432-1441.
22. Bai, G.; Feng, B.; Wang, J. B.; Pozharski, E.; Shapiro, M. Studies on ligand binding to histidine triad nucleotide binding protein 1. *Bioorg Med Chem.* 2010, 18, 6756-6762.
23. Dawadi, S.; Viswanathan. K.; Boshoff, H. I.: Barry, C. E.; Aldrich, C. C. Investigation and conformational analysis of fluorinated nucleoside antibiotics targeting siderophore biosynthesis. *J Org Chem.* 2015, 80, 4835-4850.
24. Gruber, B. A. Leonard N. J. Dynamic and static quenching of 1,N6-ethenoadenine dinucleotide and in 1,N6-etheno-9-(3-(indol-3-yl)propyl) adenine. *Proc Natl Acad Sci USA.* 1975, 72, 3966-3969.
25. Dolot, R.; Ozga, M.; Wlodarczyk, A.; Krakowiak A.; Nawrot, B. A new crystal form of human histidine triad nucleotide-binding protein 1 (hHINT1) in complex with adenosine 5'-monophosphate at 1.38 Å resolution. *Acta Crystallogr Sect F Struct Biol Cryst Commun.* 2012, 68, 883-888.
26. Snyder, P. W.; Mecinovic, J.; Moustakas, D. T.; Thomas S. W.; Harder, M.; Mack, E. T.; Lockett, M. R.; Héroux, A.; Sherman, W.; Whitesides, G. M. Mechanism of the hydrophobic effect in the biomolecular recognition of arylsulfonamides by carbonic anhydrase. *Proc Natl Acad Sci USA.* 2011, 108, 17889-17894.
27. Breiten, B.; Lockett, M. R.; Sherma, W.; Fujita, S.; Al-Sayah, M.; Lange, H.; Bowers, C. M.; Heroux, A.; Krilov, G.; Whitesides, G. M. Water networks contribute to enthalpy/entropy compensation in protein-ligand binding. *J Am Chem Soc.* 2013, 135, 15579-15584.
28. Persch, E.; Dumele, O.; Diederich, F. Molecular recognition in chemical and biological systems. *Angew Chem Int Ed Engl.* 2015, 54, 3290-3327.

Various modifications and many further embodiments thereof, in addition to those shown and described herein, will become apparent to those skilled in the art from the full contents of this document, including references to the scientific and patent literature cited herein. The subject matter herein contains important information, exemplification and guidance that can be adapted in its various embodiments and equivalents thereof.

The terms and expressions which have been employed are used as terms of description and not of limitation, and there is no intention that in the use of such terms and expressions of excluding any equivalents of the features shown and described or portions thereof, but it is recognized that various modifications are possible. Thus, it should be understood that although various embodiments have been specifically disclosed herein, modification and variation of the concepts herein disclosed may be resorted to by those of ordinary skill in the art, and that such modifications and variations are considered to be within the scope of the various embodiments defined by the appended claims.

Values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1 to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading may occur within or outside of that particular section. Furthermore, all publications, patents, and patent documents referred to in this document are incorporated by reference herein in their entirety, as though individually incorporated by reference.

In the methods described herein, the steps can be carried out in any order without departing from the principles described herein, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range.

What is claimed is:

1. A compound of formula I:

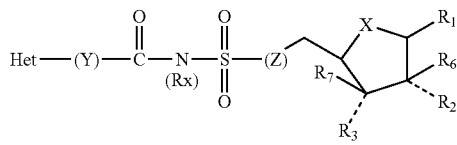

wherein $R_1$ is guanine, 3-deazadenine or [6,7-imino(alkylene)] adenine, optionally substituted by 1, 2 or 3 U wherein each U is independently halo, hydroxy, $(C_1$-$C_6)$alkyl, $(C_3$-$C_6)$cycloalkyl, $(C_1$-$C_6)$alkoxy, $(C_3$-$C_6)$ cycloalkyloxy, $(C_1$-$C_6)$alkanoyl, $(C_1$-$C_6)$alkanoyloxy, trifluoromethyl, hydroxy$(C_1$-$C_6)$alkyl, —$(CH_2)_{1-4}$P(=O)$(OR_w)_2$ aryl, aryl$(C_1$-$C_6)$alkyl, or $Nr_xR_y$;

$R_2$, $R_3$, $R_6$ and $R_7$ are each independently hydrogen, halo, hydroxy, $(C_1$-$C_6)$alkyl, $(C_3$-$C_6)$cycloalkyl, $(C_1$-$C_6)$alkoxy, $(C_3$-$C_6)$cycloalkyloxy, $(C_1$-$C_6)$alkanoyl, $(C_1$-$C_6)$alkanoyloxy, trifluoromethyl, azido, cyano, —N$(R_z)$C(=O)N$(R_{aa})(R_{ab})$, —N$(R_z)$C(=O)O$R_{ac}$, or NR$_{ad}$R$_{ae}$, provided that one of $R_2$ and $R_6$ is hydroxy, halo, $(C_1$-$C_6)$alkoxy, $(C_3$-$C_6)$cycloalkyloxy, trifluoromethyl, cyano, or $Nr_{ad}R_{ae}$;

X is oxy, thio, or methylene;

Z is N(Rx) or O;

Y is $(C_1$-$C_9)$alkyl, that optionally contains 1-3 CH=CH moieties and/or 1-3 —O-, N(Rx) or —SO— moieties;

each $R_w$ is independently hydrogen or $(C_1$-$C_6)$alkyl;

$R_x$, $R_y$ and Rz are each independently hydrogen, $(C_1$-$C_6)$ alkyl, $(C_3$-$C_6)$cycloalkyl, phenyl, benzyl, phenethyl, or $(C_1$-$C_6)$alkanoyl; or $R_x$ and $R_y$ together with the nitrogen to which they are attached are pyrrolidino, piperidino or morpholino;

$R_{aa}$ and $R_{ab}$ are each independently hydrogen, $(C_1$-$C_6)$ alkyl, $(C_3$-$C_6)$cycloalkyl, phenyl, benzyl, or phenethyl; or $R_{aa}$ and $R_{ab}$ together with the nitrogen to which they are attached are pyrrolidino, piperidino or morpholino;

$R_{ac}$, $R_{ad}$, and $R_{ae}$ are independently hydrogen, $(C_1$-$C_6)$ alkyl, $(C_3$-$C_6)$cycloalkyl, phenyl, benzyl, or phenethyl;

wherein any $(C_1$-$C_6)$alkyl of $R_1$, $R_2$, $R_3$, $R_6$, $R_7$, $R_w$, $R_x$, $R_y$, $R_z$, $R_{aa}$, $R_{ab}$, $R_{ac}$, $R_{ad}$, and $R_{ae}$ is optionally substituted with one or more halo, hydroxy, $(C_1$-$C_6)$ alkoxy, $(C_3$-$C_6)$cycloalkyloxy, $(C_1$-$C_6)$alkanoyl, $(C_1$-$C_6)$alkanoyloxy, trifluoromethyl, azido, cyano, oxo (=O), $(C_1$-$C_6)$alkyl, $(C_3$-$C_6)$cycloalkyl, $(C_3$-$C_6)$cycloalkyl$(C_1$-$C_6)$alkyl, $(C_1$-$C_6)$alkyl-S—$(C_1$-$C_6)$alkyl-, aryl, aryl$(C_1$-$C_6)$alkyl, or Het $(C_1$-$C_6)$alkyl, or $NR_{aj}R_{ak}$; wherein each $R_{aj}$ and $R_{ak}$ is independently hydrogen, $(C_1$-$C_6)$alkyl, $(C_3$-$C_6)$cycloalkyl, phenyl, benzyl, or phenethyl;

wherein Het is $(C_1$-$C_6)$ alkyl or

Het-Y— is $(C_1$-$C_6)$alkyl substituted with a pyridyl, indolyl, isoindolyl, furyl, thienyl, pyrrolyl, benzofuranyl, benzothienyl, imidazolyl, thiazoyl, pyrrolidinyl, piperidinyl, piperazinyl, or morpholino ring, which ring is optionally substituted with one or more substituents selected from the group consisting of halo, hydroxy, (C1-C6)alkyl, (C3-C6)cycloalkyl, (C1-C6)alkoxy, (C3-C6)cycloalkyloxy, (C1-C6)alkanoyl, (C1-C6)alkanoyloxy, trifluoromethyl, trifluoromethoxy, nitro, cyano, and amino;

or a pharmaceutically acceptable salt thereof.

2. The compound of claim 1 wherein X is O.
3. The compound of claim 1 wherein Z is O or N($R_x$).
4. The compound of claim 3 wherein Z is N(H).
5. The compound of claim 1 wherein $R_x$ is H.
6. The compound of claim 1 wherein Y is $(C_1$-$C_6)$alkyl.
7. The compound of claim 1 wherein Het is indolyl.
8. The compound of claim 1 where $R_1$ is adenine, guanine or 6,7-iminoalkenyl adenine.
9. A compound of the formula:

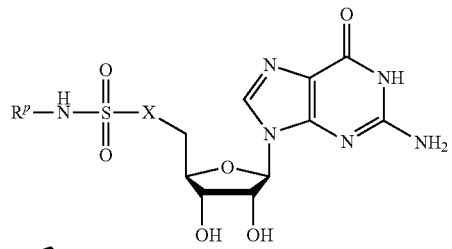

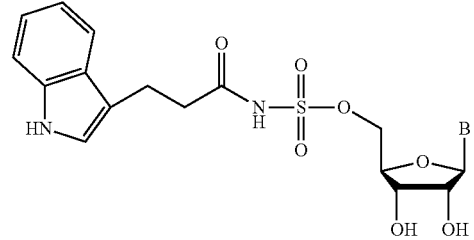

wherein B = 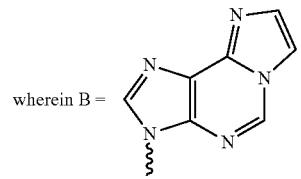

wherein $R^p$ is indole propanoyl and X is O; $R^p$ is butanoyl and X is O; $R^p$ is indole propanoyl and X is NH, or a pharmaceutically acceptable salt thereof.

* * * * *